United States Patent
Ni et al.

(10) Patent No.: US 7,440,803 B2
(45) Date of Patent: Oct. 21, 2008

(54) CLOSED LOOP IMPEDANCE-BASED CARDIAC RESYNCHRONIZATION THERAPY SYSTEMS, DEVICES, AND METHODS

(75) Inventors: Quan Ni, Shoreview, MN (US); Jiang Ding, Maplewood, MN (US); Yinghong Yu, Shoreview, MN (US); Douglas R. Daum, Woodbury, MN (US); Julio C. Spinelli, Shoreview, MN (US); Jeffrey E. Stahmann, Ramsey, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 11/264,941

(22) Filed: Nov. 2, 2005

(65) Prior Publication Data

US 2006/0271119 A1    Nov. 30, 2006

Related U.S. Application Data

(63) Continuation of application No. 11/136,894, filed on May 25, 2005.

(51) Int. Cl.
*A61N 1/365* (2006.01)
(52) U.S. Cl. .......................................... 607/9
(58) Field of Classification Search .............. 607/8, 607/9
See application file for complete search history.

(56) References Cited

U.S. PATENT DOCUMENTS

| | | | |
|---|---|---|---|
| 5,626,623 A | 5/1997 | Kieval et al. |
| 5,788,643 A | 8/1998 | Feldman |
| 6,070,100 A | 5/2000 | Bakels et al. |
| 6,076,015 A | 6/2000 | Hartley et al. |
| 6,219,579 B1 | 4/2001 | Bakels et al. |
| 6,223,082 B1 | 4/2001 | Bakels et al. |
| 6,238,420 B1 | 5/2001 | Bakels et al. |
| 6,278,894 B1 | 8/2001 | Salo et al. |
| 6,280,389 B1 | 8/2001 | Ding et al. |
| 6,751,503 B1 | 6/2004 | Kroll |
| 6,751,504 B2 | 6/2004 | Fishler |

(Continued)

OTHER PUBLICATIONS

Abe et al. Asynchronous Relaxation of the Ischemic Left Ventricle. Japanese Circulation Journal. Jan. 1982; 46(1) 103-112.*

(Continued)

*Primary Examiner*—Carl H. Layno
*Assistant Examiner*—Eric D Bertram
(74) *Attorney, Agent, or Firm*—Schwegman, Lundberg & Woessner, P.A.

(57) ABSTRACT

This document discusses, among other things, systems, devices, and methods measure an impedance and, in response, adjust an atrioventricular (AV) delay or other cardiac resynchronization therapy (CRT) parameter that synchronizes left and right ventricular contractions. A first example uses parameterizes a first ventricular volume against a second ventricular volume during a cardiac cycle, using a loop area to create a synchronization fraction (SF). The CRT parameter is adjusted in closed-loop fashion to increase the SF. A second example measures a septal-freewall phase difference (PD), and adjusts a CRT parameter to decrease the PD. A third example measures a peak-to-peak volume or maximum rate of change in ventricular volume, and adjusts a CRT parameter to increase the peak-to-peak volume or maximum rate of change in the ventricular volume.

14 Claims, 16 Drawing Sheets

U.S. PATENT DOCUMENTS

| | | |
|---|---|---|
| 6,754,530 B2 | 6/2004 | Bakels et al. |
| 6,885,889 B2 | 4/2005 | Chinchoy |
| 7,127,289 B2 | 10/2006 | Yu et al. |
| 7,283,873 B1 * | 10/2007 | Park et al. ............ 607/16 |
| 2002/0002389 A1 | 1/2002 | Bradley et al. |
| 2003/0100925 A1 | 5/2003 | Pape et al. |
| 2003/0204212 A1 * | 10/2003 | Burnes et al. ............ 607/17 |
| 2003/0216657 A1 | 11/2003 | Holmstrom et al. |
| 2004/0015081 A1 | 1/2004 | Kramer et al. |
| 2004/0015196 A1 | 1/2004 | Holstrom et al. |
| 2004/0049238 A1 | 3/2004 | Jarverud |
| 2004/0078058 A1 | 4/2004 | Holmstrom et al. |
| 2005/0043895 A1 | 2/2005 | Schechter |
| 2005/0049646 A1 | 3/2005 | Czygan et al. |
| 2005/0182447 A1 | 8/2005 | Schecter |
| 2006/0271121 A1 | 11/2006 | Ding et al. |
| 2007/0043394 A1 | 2/2007 | Zhang et al. |
| 2007/0129781 A1 | 6/2007 | Yu et al. |

OTHER PUBLICATIONS

Yinghong, Yu et al., "A Cardiac Resynchronization System Employing Mechanical Measurement of Cardiac Walls", U.S. Appl. No. 11/549,676, filed Oct. 16, 2006, 28 pages.

Yu, Yinghong, et al., "Biventricular mechnical asynchrony predicts hemodynamic effects of uni- and biventricular pacing", *Am J Physiol Heart Circ Physiol*, vol. 285, (2003), H2788-H2796.

Yu, C.-M., et al., "High Prevalence of Left Ventricular Systolic and Diastolic Asynchrony in Patients With Congestive Heart Failure and Normal QRS Duration", *Heart*, vol. 89, (2003), 54-60.

Zhang, Yunlong, "Intracardiac Impendance and its applications", U.S. Appl. No. 11/208,922, filed Aug. 22, 2005, 36 Pgs.

"Non-Final Office Action mailed Apr. 26, 2007 in U.S. Appl. No. 11/136,894 ", 11 pages.

* cited by examiner

CLOSED LOOP IMPEDANCE-BASED CARDIAC RESYNCHRONIZATION THERAPY SYSTEMS, DEVICES, AND METHODS

CROSS REFERENCE TO RELATED APPLICATIONS

This patent application is a continuation of Jiang Ding et al. U.S. patent application Ser. No. 11/136,894, entitled CLOSED LOOP IMPEDANCE-BASED CARDIAC RESYNCHRONIZATION THERAPY SYSTEMS, DEVICES, AND METHODS, filed on May 25, 2005 and assigned to Cardiac Pacemakers, Inc., and which is incorporated by reference in its entirety.

TECHNICAL FIELD

This patent document pertains generally to cardiac function management devices, and more particularly, but not by way of limitation, to closed loop resynchronization therapy systems, devices, and methods.

BACKGROUND

When functioning properly, the human heart maintains its own intrinsic rhythm. Its sinoatrial node generates intrinsic electrical cardiac signals that depolarize the atria, causing atrial heart contractions. Its atrioventricular node then passes the intrinsic cardiac signal to depolarize the ventricles, causing ventricular heart contractions. These intrinsic cardiac signals can be sensed on a surface electrocardiogram (ECG) obtained from electrodes placed on the patient's skin, or from electrodes implanted within the patient's body. The surface ECG waveform, for example, includes artifacts associated with atrial depolarizations ("P-waves") and those associated with ventricular depolarizations ("QRS complexes").

A normal heart is capable of pumping adequate blood throughout the body's circulatory system. However, some people have irregular cardiac rhythms, referred to as cardiac arrhythmias. Moreover, some patients have poor spatial coordination of heart contractions. Some patients may have both irregular rhythms and poor spatial coordination of heart contractions. In either of these cases, diminished blood circulation may result. For such patients, a cardiac function management system may be used to improve the rhythm and/or spatial coordination of heart contractions. Such systems are often implanted in the patient and deliver therapy to the heart, such as electrical stimulation pulses that evoke or coordinate heart chamber contractions.

One problem faced by physicians treating cardiovascular patients is the treatment of congestive heart failure (also referred to as "CHF"). Congestive heart failure, which can result from a number of causes such as long-term hypertension, is a condition in which the muscle in the walls of at least one of the right and (more typically) the left side of the heart deteriorates. By way of example, suppose the muscle in the walls of left side of the heart deteriorates. As a result, the left atrium and left ventricle become enlarged, and that heart muscle displays less contractility. This decreases cardiac output of blood through the circulatory system which, in turn, may result in an increased heart rate and less resting time between heartbeats. The heart consumes more energy and oxygen, and its condition typically worsens over a period of time.

In the above example, as the left side of the heart becomes enlarged, the intrinsic electrical heart signals that control heart rhythm may also be affected. Normally, such intrinsic signals originate in the sinoatrial (SA) node in the upper right atrium, traveling through electrical pathways in the atria and depolarizing the atrial heart tissue such that resulting contractions of the right and left atria are triggered. The intrinsic atrial heart signals are received by the atrioventricular (AV) node which, in turn, triggers a subsequent ventricular intrinsic heart signal that travels through specific electrical pathways in the ventricles and depolarizes the ventricular heart tissue such that resulting contractions of the right and left ventricles are triggered substantially simultaneously.

In the above example, where the left side of the heart has become enlarged due to congestive heart failure, however, the conduction system formed by the specific electrical pathways in the ventricle may be affected, as in the case of left bundle branch block (LBBB). As a result, ventricular intrinsic heart signals may travel through and depolarize the left side of the heart more slowly than in the right side of the heart. As a result, the left and right ventricles do not contract simultaneously, but rather, the left ventricle contracts after the right ventricle. This reduces the pumping efficiency of the heart. Moreover, in LBBB, for example, different regions within the left ventricle may not contract together in a coordinated fashion.

Cardiac function management systems include, among other things, pacemakers, also referred to as pacers. Pacers deliver timed sequences of low energy electrical stimuli, called pace pulses, to the heart, such as via an intravascular lead wire or catheter (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly. Such pacers may also coordinate atrial and ventricular contractions to improve pumping efficiency.

Cardiac function management systems also include cardiac resynchronization therapy (CRT) devices for coordinating the spatial nature of heart depolarizations for improving pumping efficiency, such as for patients having CHF. For example, a CRT device may deliver appropriately timed pace pulses to different locations of the same heart chamber to better coordinate the contraction of that heart chamber, or the CRT device may deliver appropriately timed pace pulses to different heart chambers to improve the manner in which these different heart chambers contract together, such as to synchronize left and right side contractions.

Cardiac function management systems also include defibrillators that are capable of delivering higher energy electrical stimuli to the heart. Such defibrillators include cardioverters, which synchronize the delivery of such stimuli to sensed intrinsic heart activity signals. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock, also referred to simply as a "shock." The countershock interrupts the tachyarrhythmia, allowing the heart to reestablish a normal rhythm for the efficient pumping of blood. In addition to pacers, CRT devices, and defibrillators, cardiac function management systems also include devices that combine these functions, as well as monitors, drug delivery devices, and any other implantable or external systems or devices for diagnosing or treating the heart.

The present inventors have recognized a need for improved techniques for determining the degree of asynchrony (also sometimes referred to as dyssynchrony) between the left and right sides of the heart of a CHF patient.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
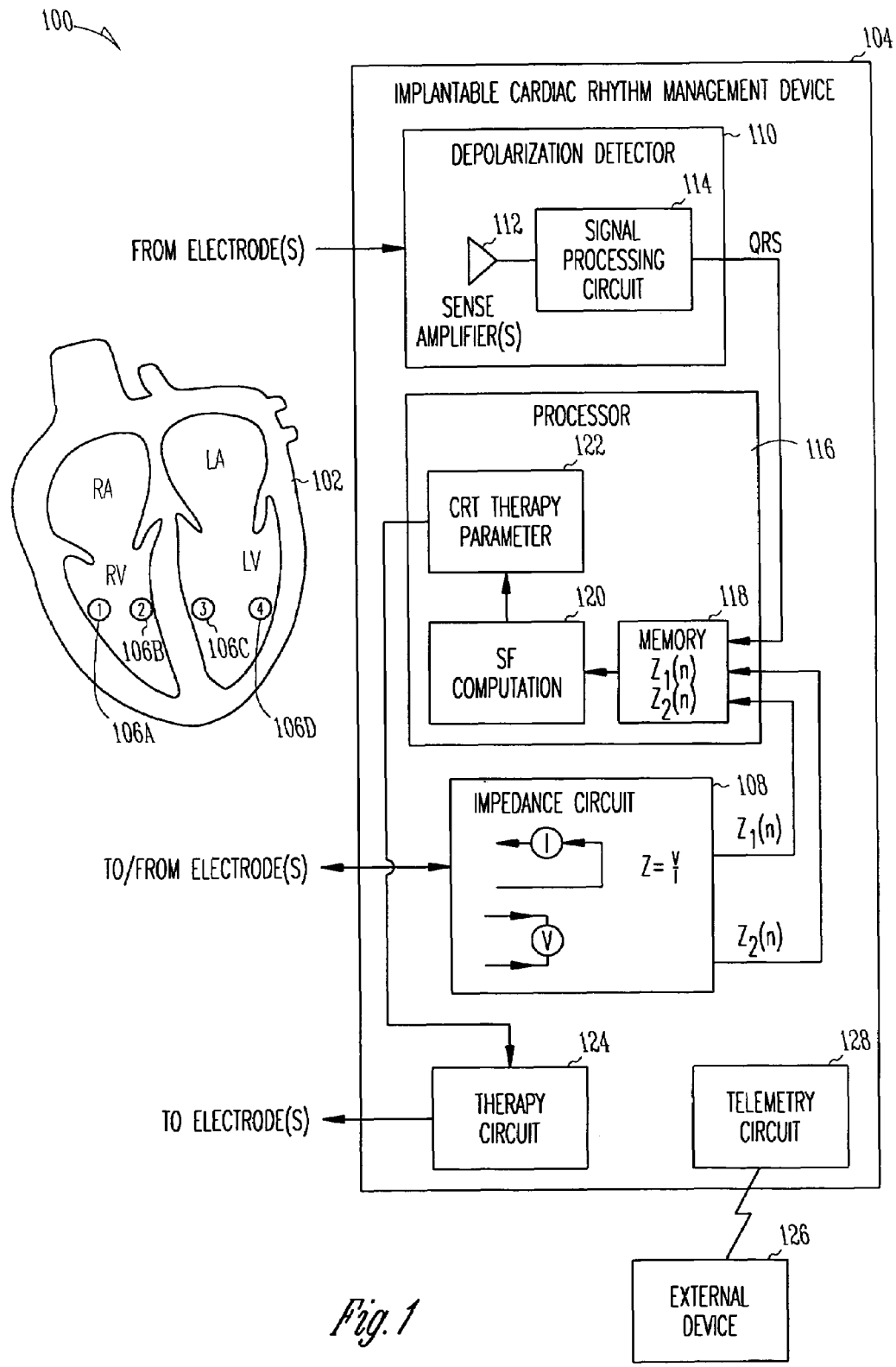
FIG. 1 is a schematic diagram illustrating generally one example of portions of a system and portions of an environment with which it is used.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

The present inventors have recognized a need for improved techniques for, among other things, determining the degree of asynchrony between the left and right sides of the heart of a CHF patient. For example, techniques that detect electrical depolarizations (e.g., QRS complexes) at the left and right sides of the heart to indicate the synchrony between the two sides of the heart are often not a good indicator of the actual mechanical synchrony between left and right ventricular heart contractions. Another technique, for example, uses a pressure sensor to determine synchrony between left and right ventricular contractions. However, such a pressure-sensing technique typically requires a customized intracardiac lead that specially includes a pressure sensor. This adds expense and complexity to an implantable cardiac function management system.

This document describes, among other things, examples of cardiac function management systems, devices, and methods that measure an impedance, such as to determine or infer synchrony between right and left ventricles, or to provide another control parameter for adjusting cardiac resynchronization (CRT) therapy. In further examples, the impedance-derived information is used to automatically adjust one or more cardiac resynchronization therapy (CRT) parameters, such as on a beat-by-beat basis in a closed-loop feedback configuration, to provide improved spatial coordination of heart contractions (without necessarily affecting the actual heart rate of such heart contractions). The CRT therapy typically improves ventricular mechanical synchrony, stroke volume, coordination, etc. by manipulating the electrical activation sequence, such as by delivering appropriate stimulations to desired locations.

EXAMPLE 1

FIG. 1 is a schematic diagram illustrating generally one example of portions of a system 100 and portions of an environment with which it is used, including a heart 102. In this example, the system 100 includes an implantable cardiac function management device 104. In one example, the device 104 is coupled to the heart 102 using one or more intravascular or other leadwires. The leadwires provide electrodes 106 in association with the heart 102. FIG. 1 illustrates an example that includes a first electrode 106A that is located at or near a right ventricular freewall, a second electrode 106B that is located at or near a right ventricular septum, a third electrode 106C that is located at or near a left ventricular septum, and a fourth electrode 106D that is located at or near a left ventricular freewall. This particular electrode configuration of FIG. 1 is useful for providing conceptual clarity, however, other possibly more practical electrode configurations will be discussed further below.

In FIG. 1, device 104 includes an impedance circuit 108 for measuring a first impedance indicative of right ventricular volume (e.g., between the first electrode 106A and the second electrode 106B) and a second impedance indicative of a left ventricular volume (e.g., between the third electrode 106C and the fourth electrode 106D). The first and second impedances are modulated as the right and left ventricles contract and expand. In one example, this impedance modulation is used to detect asynchrony between the left and right ventricular heart contractions, as discussed below.

In the example of FIG. 1, a depolarization detector circuit 110 detects intrinsic electrical heart depolarizations, such as by using one or more sense amplifiers 112 or signal processing circuits 114 to detect QRS complexes, which are depolarizations corresponding to ventricular heart contractions. The time interval between two successive QRS complexes can be used to define a cardiac cycle. In one example, the impedance modulation is monitored over a cardiac cycle for making the asynchrony determination, as discussed below.

In the example of FIG. 1, a microprocessor, microcontroller, or other processor circuit 116 executes, interprets, or otherwise performs instructions to provide computational ability. The impedance circuit 108 provides a sampled data right ventricular impedance waveform $Z_1(n)$ and a sampled data left ventricular impedance waveform $Z_2(n)$ to the processor 116 to be stored in a memory circuit 118 located within or external to the processor 116. In one example, the processor 116 uses a cardiac cycle's worth of the right ventricular impedance waveform $Z_1(n)$ and of the left ventricular impedance waveform $Z_2(n)$ to compute an indication of the degree of asynchrony (or, conversely, of synchrony) between the right and left ventricles, as discussed below. In one example, this indication is provided by a synchrony fraction (SF) computation module 120 comprising instructions that are executed by the processor 116. In a further example, the SF or other indication of asynchrony or synchrony is used to control at least one cardiac resynchronization therapy (CRT) parameter 122. The CRT parameter 122, in turn, controls one or more aspects of the delivery of stimulation pulses or other CRT therapy by therapy circuit 124, which is coupled to electrodes associated with the heart 102, such as electrodes 106 or other electrodes.

Impedance measurement circuit 108 can be implemented in a number of different ways, such as by using circuits and techniques similar to those used for detecting transthoracic impedance, an example of which is described in Hartley et al. U.S. Pat. No. 6,076,015, which is incorporated herein by reference in its entirety, including its description of impedance measurement. The Hartley et al. U.S. Pat. No. 6,076,015 describes, among other things, injecting a four-phase carrier signal through two electrodes, such as the present electrodes 106A-B, or the present electrodes 106C-D. Hartley et al. uses first and third phases that are +320 microampere pulses, which are 20 microseconds long. The second and fourth phases are −320 microampere pulses that are 20 microseconds long. The four phases are repeated at 50 millisecond intervals to provide a carrier test current signal from which a responsive voltage can be measured. However, different excitation frequency, amplitude, and pulse duration can also be used. These impedance testing parameters are typically selected to be subthreshold, that is, they use an energy that avoids evoking a responsive heart contraction. These impedance testing parameters are also typically selected to avoid introducing a visible artifact on an ECG signal monitor of intrinsic heart signals.

The Hartley et al. U.S. Pat. No. 6,076,015 describes a suitable exciter circuit for delivering such a test current stimulus (however, the present system can alternatively use other suitable circuits, including an arbitrary waveform generator that is capable of operating at different frequencies or of mixing different frequencies to generate an arbitrary waveform). It also describes a suitable signal processing circuit for measuring a responsive voltage, such as between the present electrodes 106A-B, or between the present electrodes 106C-D. In one example, the signal processing circuit includes a preamplifier, demodulator, and bandpass filter for extracting the impedance data from the carrier signal, before conversion into digital form by an A/D converter. Further processing is performed digitally, and is typically performed differently in the present system 100 than in the Hartley et al. U.S. Pat. No. 6,076,015. For example, the present system typically includes a digital filter that passes frequency components of the measured impedance signal that are close to the frequency of heart contractions. The present digital filter typically attenuates other lower or higher frequency components of the measured impedance signal.

Figure 2:
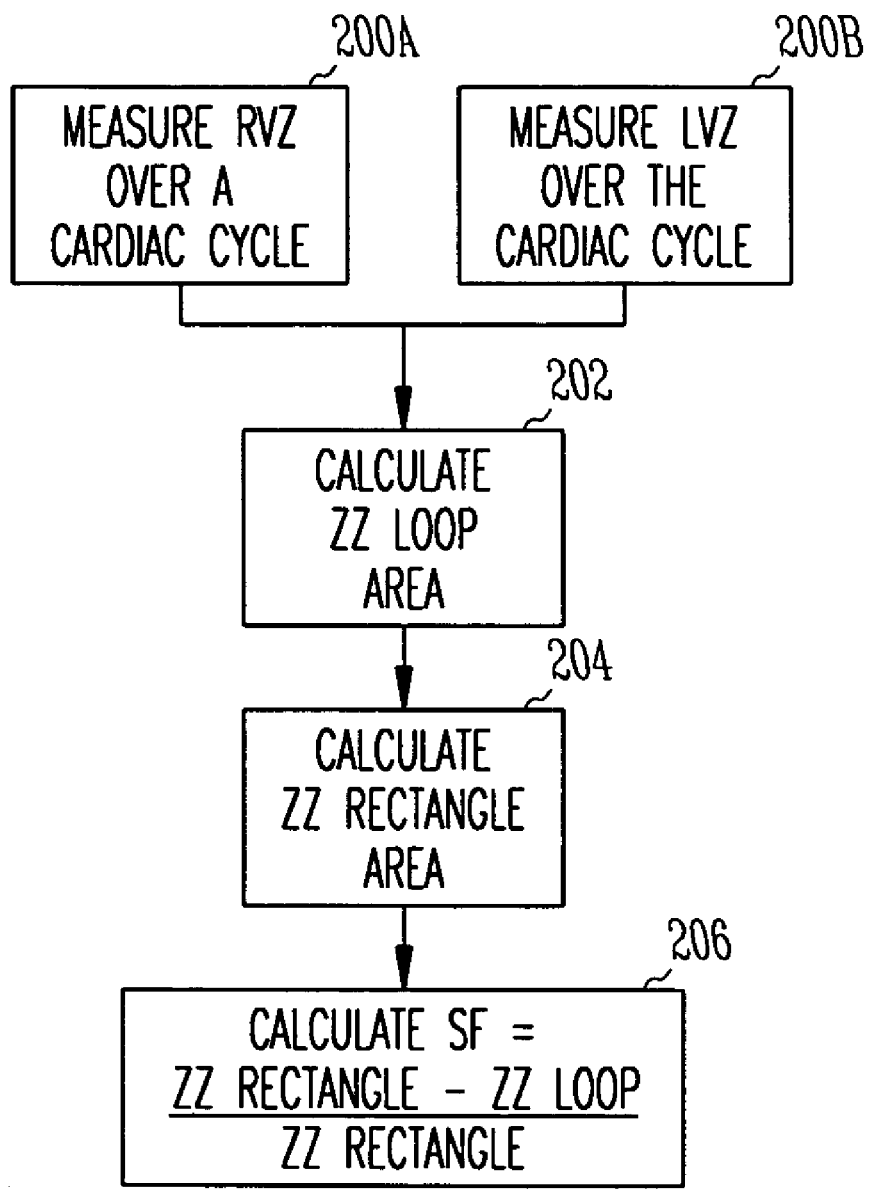
FIG. 2 is a flow chart illustrating generally one example of a technique for determining a degree of synchrony or asynchrony between left and right ventricular contractions of a heart.

FIG. 2 is a flow chart illustrating generally one example of a technique for determining a degree of synchrony or asynchrony between left and right ventricular contractions of a heart. At 200A, a right ventricular impedance ("RVZ" or "$Z_1$") is monitored over a cardiac cycle, such as by injecting a subthreshold (i.e., non-contraction-evoking) current and measuring a responsive voltage (e.g., using electrodes 106A-B). Concurrent with 200A, at 200B, a left ventricular impedance ("LVZ" or "$Z_2$") is monitored over the same cardiac cycle, such as by injecting a subthreshold current and measuring a responsive voltage (e.g., using electrodes 106C-D).

Figure 3A:
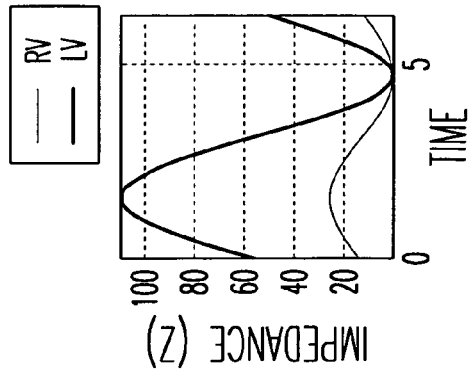
FIG. 3A is a conceptual (not real data) impedance vs. time graph of RVZ and LVZ over the same cardiac cycle for the case of synchrony between right and left ventricular contractions.
Figure 4A:
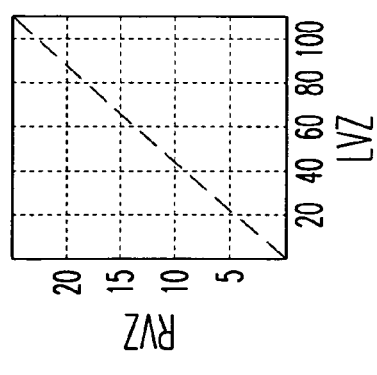
FIG. 4A is a graph (corresponding to FIG. 3A) of right ventricular impedance (RVZ) vs. left ventricular impedance (LVZ) for the case of synchrony between right and left ventricular contractions.
Figure 3B:
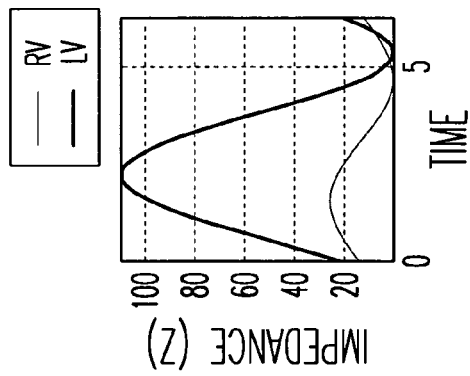
FIG. 3B is a conceptual (not real data) impedance vs. time graph of RVZ and LVZ over the same cardiac cycle for the case of mild asynchrony between right and left ventricular contractions.
Figure 4B:
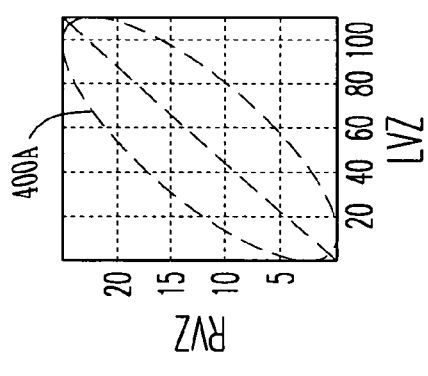
FIG. 4B is a graph (corresponding to FIG. 3B) of right ventricular impedance (RVZ) vs. left ventricular impedance (LVZ) for the case of mild asynchrony between right and left ventricular contractions.
Figure 3C:
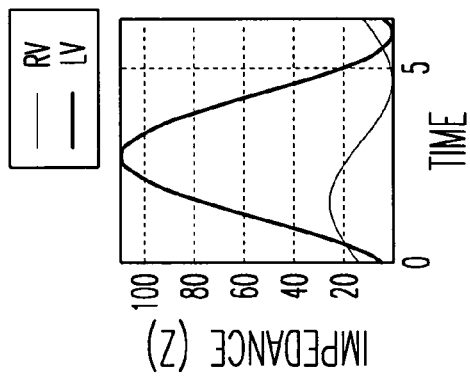
FIG. 3C is a conceptual (not real data) impedance vs. time graph of RVZ and LVZ over the same cardiac cycle for the case of severe asynchrony between right and left ventricular contractions.
Figure 4C:
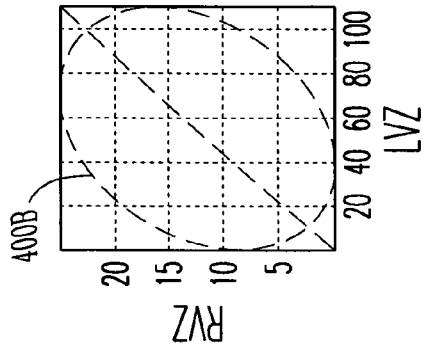
FIG. 4C is a graph (corresponding to FIG. 3C) of right ventricular impedance (RVZ) vs. left ventricular impedance (LVZ) for the case of severe asynchrony between right and left ventricular contractions.

FIGS. 3A, 3B, and 3C are conceptual (not real data) impedance vs. time graphs of RVZ and LVZ over the same cardiac cycle for the respective cases of synchrony, mild asynchrony, and severe asynchrony between right and left ventricular contractions. Corresponding to FIGS. 3A, 3B, and 3C, respectively, are the Lissajous graphs of FIGS. 4A, 4B, and 4C, which plot right ventricular impedance (RVZ) vs. left ventricular impedance (LVZ) for the respective cases of synchrony, mild asynchrony, and severe asynchrony between right and left ventricular contractions. As illustrated in FIGS. 4A, 4B, and 4C, as asynchrony increases, an interior loop area 400 swept by RVZ vs. LVZ over the cardiac cycle increases (e.g., from approximately zero in FIG. 4A for the case of synchrony).

At 202 in FIG. 2, the interior loop area 400 (as illustrated in FIG. 4) is calculated or approximated. A larger interior loop area indicates a larger degree of asynchrony. However, this value can be "normalized," if desired, such as described below with respect to 204 and 206. At 204, a ZZ Rectangle Area is calculated as $(LVZ_{maximum}-LVZ_{minimum}) \times (RVZ_{maximum}-RVZ_{minimum})$. $LVZ_{maximum}$ and $LVZ_{minimum}$ are the respective maximum and minimum values of LVZ during the cardiac cycle. $RVZ_{maximum}-RVZ_{minimum}$ are the respective maximum and minimum values of RVZ during the same cardiac cycle.

At 206, a synchrony fraction (SF) is computed as (ZZ Rectangle Area−ZZ Loop Area)÷(ZZ Rectangle Area). SF provides an indication of synchrony between right and left ventricular contractions. In theory, complete asynchrony is indicated by SF=0 and perfect synchrony is indicated by SF=1. For example, FIG. 4A illustrates SF=1, FIG. 4B illustrates SF=0.5, and FIG. 4C illustrates SF=0.2. Thus, SF provides an intuitive measure of mechanical synchrony, similar to using the commonly known ejection fraction (EF) measure of cardiac pumping function. Alternatively, an asynchrony fraction (ASF) could be computed as (1−SF). Because of the above "normalization," the SF is independent of absolute measurements of intracardiac impedance and, therefore, should not require any patient-specific calibration.

In one example, the SF, ASF, or other indication of synchrony or asynchrony is used in a closed loop system to adjust the value of one or more CRT parameters to increase SF or decrease ASF. Examples of CRT parameters that can be varied to improve synchrony include, among other things: particular cardiac electrode site(s), atrioventricular (AV) delay, interventricular delay, or intraventricular delay.

In another example, the SF, ASF, or other indication of synchrony or asynchrony is communicated from the implantable device 104 to a local or remote external device 126, such as by using a telemetry circuit included within the implantable device 104. The indication can be displayed to physician or other caregiver, such as on a computer monitor portion of the external device 126.

In another example, the SF, ASF, or other indication of synchrony or asynchrony triggers a warning when the degree of asynchrony exceeds a particular threshold value. In one example, the warning is communicated to the external device 126, as described above. In another example, the warning is communicated directly to the patient, such as by providing an audible, vibrating, or other warning indicator within the implantable device 104.

Figure 5A:
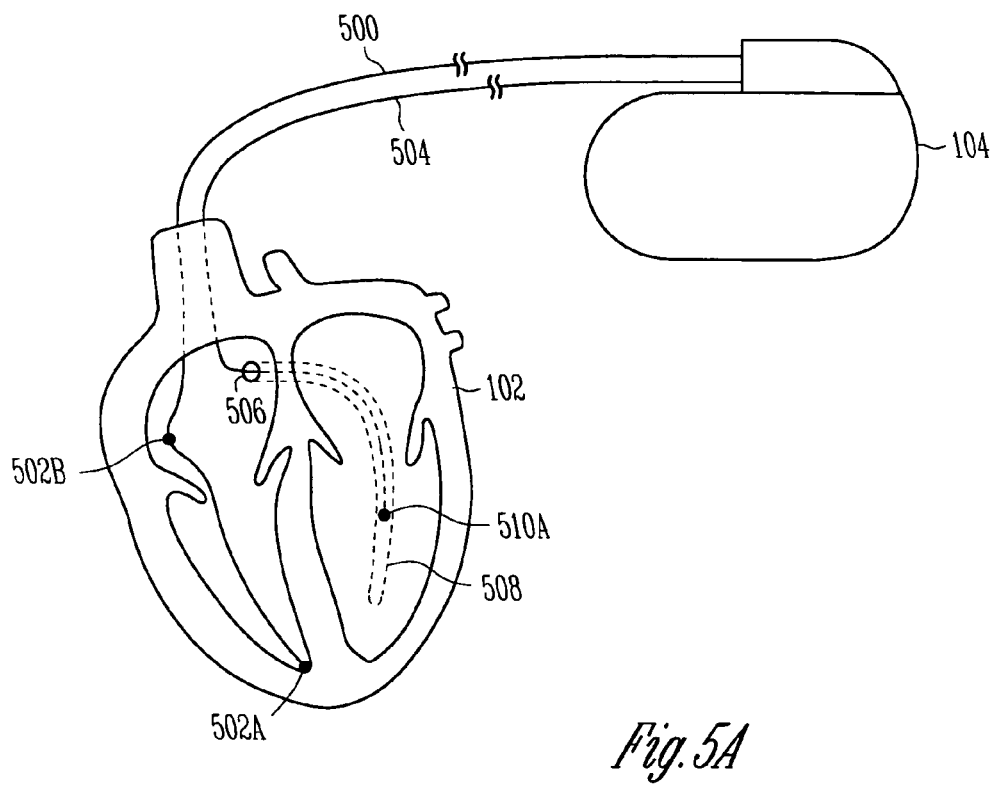
FIGS. 5A is a schematic illustration of another useful electrode configuration that can be used in conjunction with the techniques described above with respect to FIGS. 1 and 2.
Figure 5B:
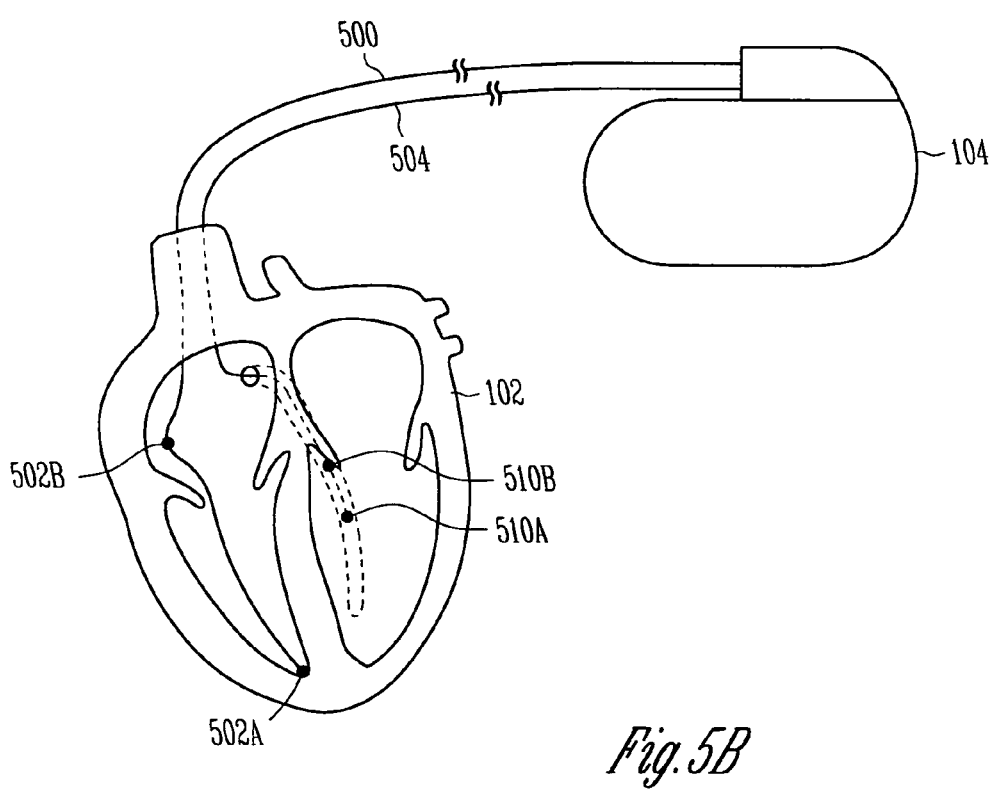
FIGS. 5B is a schematic illustration of yet another useful electrode configuration that can be used in conjunction with the techniques described above with respect to FIGS. 1 and 2.

FIG. 1 illustrated an example of an electrode configuration that is particularly useful for conceptualizing how impedance can be correlated to right and left ventricular volumes. However, other electrode configurations can also be used in conjunction with the techniques described above with respect to FIGS. 1 and 2. In one such electrode configuration, the electrodes 106B and 106C are merged into a common septal electrode. FIGS. 5A and 5B are schematic illustrations of some other useful electrode configurations that can be used in conjunction with the techniques described above with respect to FIGS. 1 and 2.

In FIG. 5A, the implantable device 104 is coupled to the heart 102 using a first lead 500 that includes a right ventricular electrode 502A located at or near the right ventricular apex. The lead 500 (or, alternatively, a separate right atrial lead) also includes a right atrial electrode 502B. In FIG. 5A, the implantable device 104 is also coupled to the heart 102 using a second lead 504 that extends into the coronary sinus 506 and into a coronary sinus vein 508 such that its distal electrode 510A is located in the coronary sinus vein 508 in association with the left ventricular freewall. The example of FIG. 5A approximates right ventricular volume using a right ventricular impedance (RVZ) obtained between the right atrial electrode 502B and the right ventricular electrode 502A. The example of FIG. 5A approximates left ventricular volume using a left ventricular impedance (LVZ) obtained between right atrial electrode 502B and left ventricular electrode 510A. This electrode configuration is practical because it potentially makes use of existing electrodes available with existing leads, however, it may be confounded slightly by other effects, such as right atrial volume fluctuations arising from right atrial contractions.

FIG. 5B is similar to FIG. 5A, however, FIG. 5B includes an additional electrode 510B on the coronary sinus lead 504. The electrode 510B is located in the mid coronary sinus at a location that is closer to the left atrium. The example of FIG. 5B approximates right ventricular volume using a right ventricular impedance (RVZ) obtained between the right atrial electrode 502B and the right ventricular electrode 502A. The example of FIG. 5B approximates left ventricular volume using a left ventricular impedance (LVZ) obtained between left atrial electrode 510B and left ventricular electrode 510A. This electrode configuration is practical because it potentially makes use of existing electrodes available with existing leads, however, it may be confounded slightly by other effects, such as right atrial volume fluctuations arising from right atrial contractions. However, this electrode configuration provides a global indication of left and right side synchrony or asynchrony, including atrial effects.

The example described above with respect to FIGS. 1-5B increases the SF by adjusting AV delay or other CRT parameter that improves the spatial coordination of heart contractions without necessarily affecting the cardiac rate. However, as the cardiac rate changes (e.g., from the patient exercising), adjusting the AV delay or other CRT parameter in a closed-loop fashion on a beat-by-beat basis may increase the SF at such other heart rates. These techniques are expected to be useful for CHF patients with or without electrical conduction disorder, because they focus on a control parameter that is not derived from intrinsic electrical heart signals, but instead use impedance indicative of a mechanical contraction parameter. For this reason, these techniques are also particularly useful for a patient with complete AV block, in which intrinsic electrical signals are not conducted to the ventricles and, therefore, CRT control techniques involving QRS width or other electrical parameters would be unavailable. For similar reasons, these techniques are useful even for patients who manifest a narrow QRS width, for whom QRS width would not be effective as a CRT control parameter.

EXAMPLE 2

Figure 6:
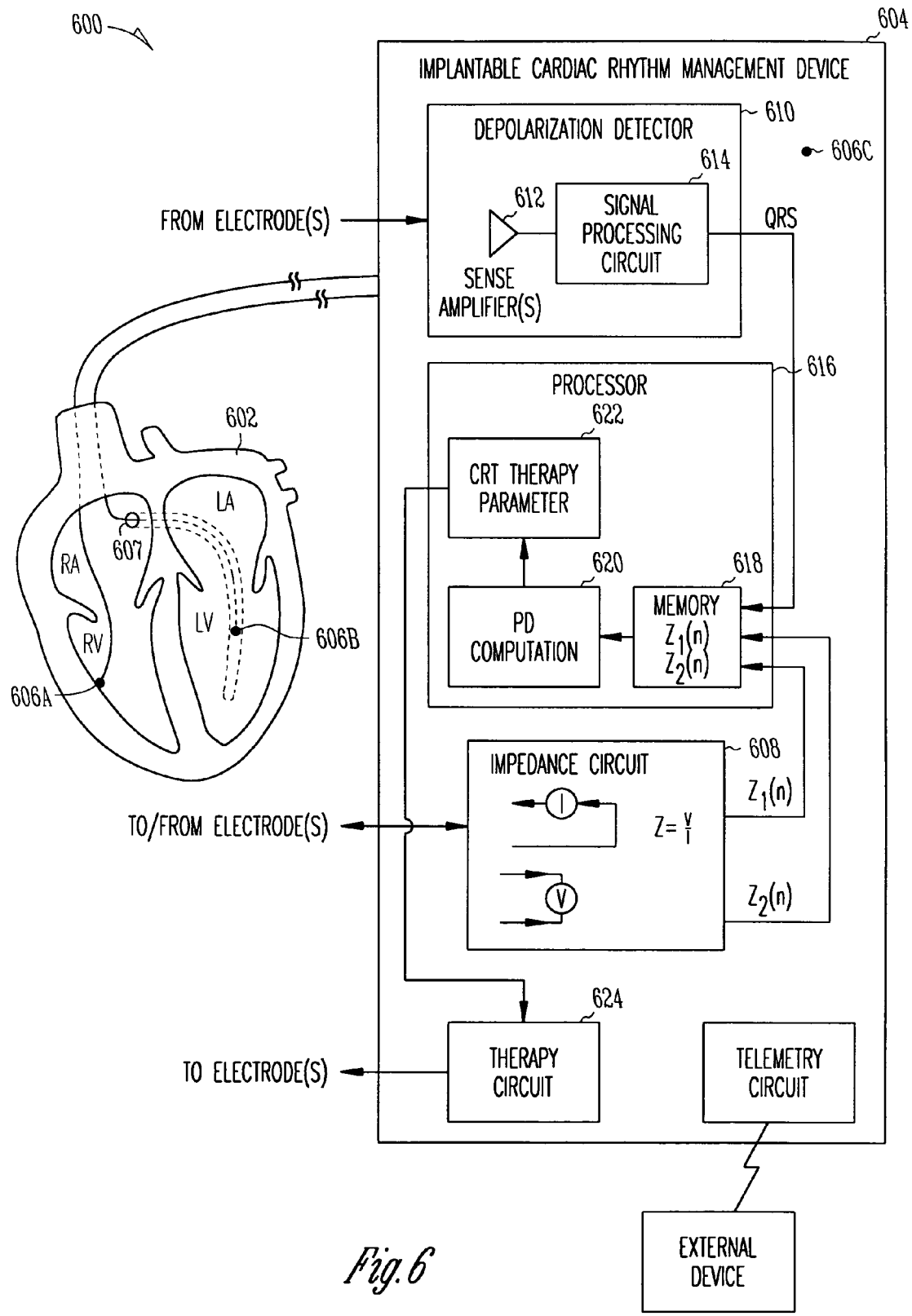
FIG. 6 is a schematic diagram illustrating generally one example of portions of a system and portions of an environment with which it is used.

FIG. 6 is a schematic diagram illustrating generally one example of portions of a system 600 and portions of an environment with which it is used, including a heart 602. In this example, the system 600 includes an implantable cardiac function management device 604. In one example, the device 604 is coupled to the heart 602 using one or more intravascular or other leads. The leads provide electrodes 606 in association with the heart 602. FIG. 6 illustrates an example that includes a first electrode 606A that is located at or near an midportion of a right ventricular freewall, a second electrode 606B that is located in association with a left ventricular freewall, such as by being introduced on an intravascular lead that is inserted into coronary sinus 607 toward a coronary sinus vein. A third electrode 606C is located on a hermetically-sealed housing ("can") of the implantable device 604 (or, alternatively, on an insulating "header" extending from the housing of the implantable device 604).

In FIG. 6, the device 604 includes an impedance circuit 608 for measuring a right ventricular impedance between the first electrode 606A and the third electrode 606C and a left ventricular impedance between the second electrode 606B and the third electrode 606C. The right and left ventricular impedances are modulated as the right and left ventricles contract and expand. In one example, this impedance modulation is used to detect asynchrony between the left and right ventricular heart contractions, as discussed below.

In the example of FIG. 6, a depolarization detector circuit 610 detects intrinsic electrical heart depolarizations, such as by using one or more sense amplifiers 612 or signal processing circuits 614 to detect QRS complexes, which are depolarizations corresponding to ventricular heart contractions. The time interval between two successive QRS complexes can be used to define a cardiac cycle. In one example, the impedance modulation is monitored over all or a particular desired portion of a cardiac cycle for making the asynchrony determination, as discussed below.

In the example of FIG. 6, a microprocessor, microcontroller, or other processor circuit 616 executes instructions to provide computational ability. The impedance circuit 608 provides a sampled data right ventricular impedance waveform $Z_1(n)$ and a sampled data left ventricular impedance waveform $Z_2(n)$ to the processor 616 to be stored in a memory circuit 618 located within or external to the processor 616. In one example, the processor 616 samples at least a portion of a cardiac cycle's worth of the right ventricular impedance waveform $Z_1(n)$ and of the left ventricular impedance waveform $Z_2(n)$ to compute an indication of the degree of asynchrony (or, conversely, of synchrony) between the right and left ventricles, as discussed below. In one example, this indication is provided by a phase difference (PD) computation module 620 comprising instructions that are executed by the processor 616. In a further example, the PD or other indication of asynchrony or synchrony is used to control at least one cardiac resynchronization therapy (CRT) parameter 622. The CRT parameter 622, in turn, controls one or more aspects of the delivery of stimulation pulses or other CRT therapy by therapy circuit 624, which is coupled to electrodes associated with the heart 602, such as electrodes 606 or other electrodes.

Impedance measurement circuit 608 can be implemented in a number of different ways, such as by using circuits and techniques similar to those used for detecting transthoracic impedance, an example of which is described in Hartley et al. U.S. Pat. No. 6,076,015, which is incorporated herein by reference in its entirety, including its description of impedance measurement. The Hartley et al. U.S. Pat. No. 6,076,015 describes, among other things, injecting a four-phase carrier signal through two electrodes, such as the present electrodes 606A and 606C, or the present electrodes 606B and 606C. Hartley et al. uses first and third phases that are +320 microampere pulses, which are 20 microseconds long. The second and fourth phases are −320 microampere pulses that are 20 microseconds long. The four phases are repeated at 50 millisecond intervals to provide a carrier test current signal from which a responsive voltage can be measured. However, different excitation frequency, amplitude, and pulse duration can also be used. These impedance testing parameters are typically selected to be subthreshold, that is, to avoid evoking a responsive heart contraction. These impedance testing parameters are also typically selected to avoid introducing a visible artifact on an ECG signal monitor.

The Hartley et al. U.S. Pat. No. 6,076,015 describes an exciter circuit for delivering such a test current stimulus (however, the present system can alternatively use other suitable circuits, including an arbitrary waveform generator that is capable of operating at different frequencies or of mixing different frequencies to generate an arbitrary waveform). It also describes a signal processing circuit for measuring a responsive voltage, such as between the present electrodes 606A and 606C, or between the present electrodes 606B and 606C. In one example, the signal processing circuit includes a preamplifier, demodulator, and bandpass filter for extracting the impedance data from the carrier signal, before conversion into digital form by an A/D converter. Further processing is performed digitally, and is performed differently in the present system 600 than in the Hartley et al. U.S. Pat. No. 6,076,015. The impedance circuit 608 of the present system typically includes a digital filter that passes frequency components of the measured impedance signal that are close to the frequency of heart contractions. The digital filter typically attenuates other lower or higher frequency components of the measured impedance signal.

Figure 7:
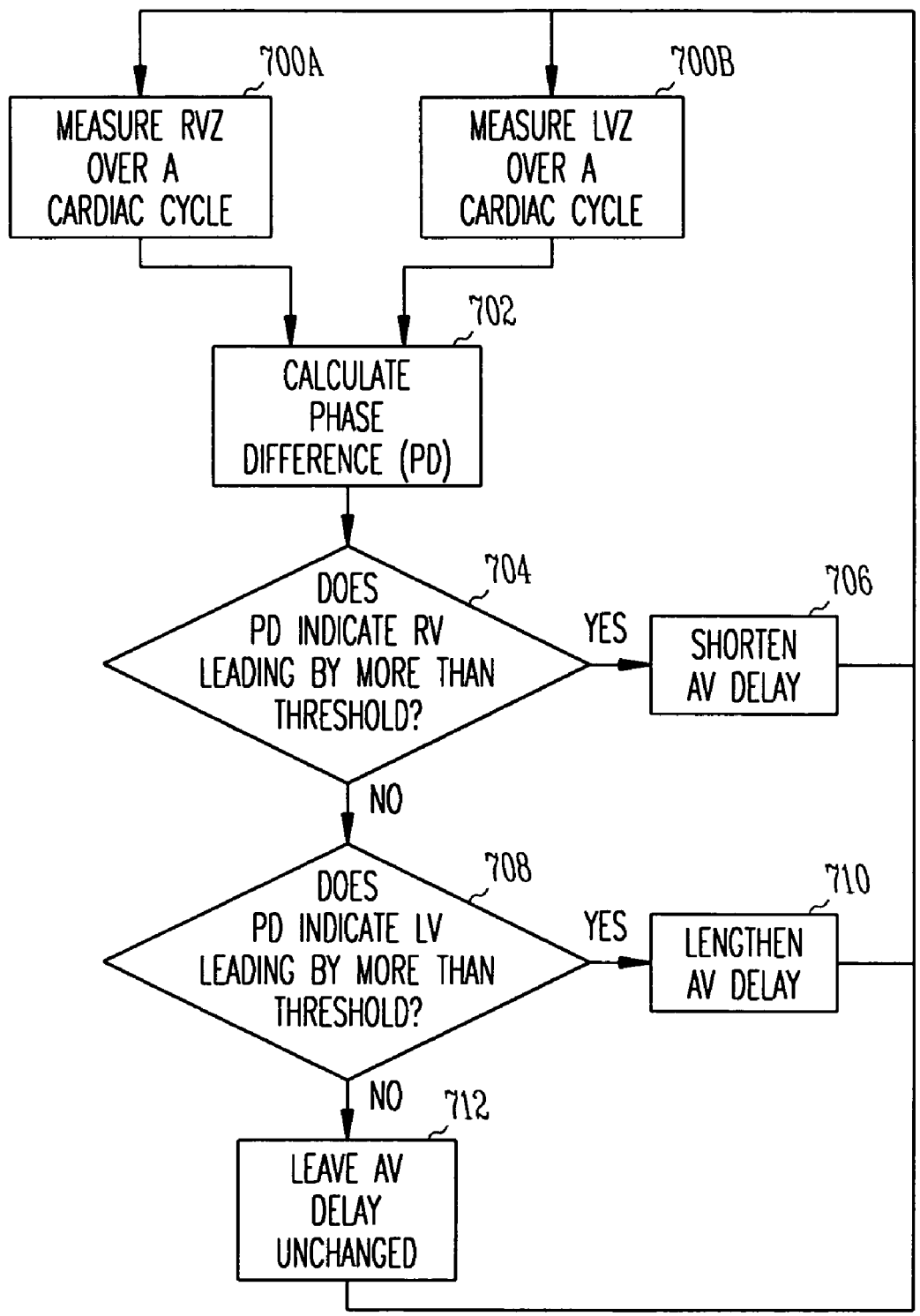
FIG. 7 is a flow chart illustrating generally one example of a technique for determining a degree of synchrony or asynchrony between left and right ventricular contractions of a heart.

FIG. 7 is a flow chart illustrating generally one example of a technique for determining a degree of synchrony or asynchrony between left and right ventricular contractions of a heart. At 700A, a right ventricular impedance (RVZ) is monitored over a cardiac cycle, such as by injecting a subthreshold (i.e., non-contraction-evoking) current (e.g., between electrodes 606A and 606C) and measuring a responsive voltage (e.g., using electrodes 606A and 606C). Concurrent with 700A, at 700B, a left ventricular impedance (LVZ) is monitored over the same cardiac cycle, such as by injecting a subthreshold current (e.g., between electrodes 606B and 606C) and measuring a responsive voltage (e.g., using electrodes 606B and 606C).

At 702, a phase difference (PD) between the right and left ventricular contractions is calculated using the RVZ and LVZ. In one embodiment, the phase difference is calculated by measuring a time difference between the same artifact on each of the RVZ and LVZ signals. In one example, a zero-cross detector detects a like zero-crossing artifact in each of the RVZ and LVZ signals, and PD is then calculated as the time difference between occurrences of these two like zero-crossings. In another example, a peak-detector detects a like peak artifact in each of the RVZ and LVZ signals, and PD is then calculated as the time difference between occurrences of these two like peaks. In yet another example, a level-detector detects a like level in each of the RVZ and LVZ signals, and PD is then calculated as a time difference between the occurrences of these two like signal levels.

Figure 8:
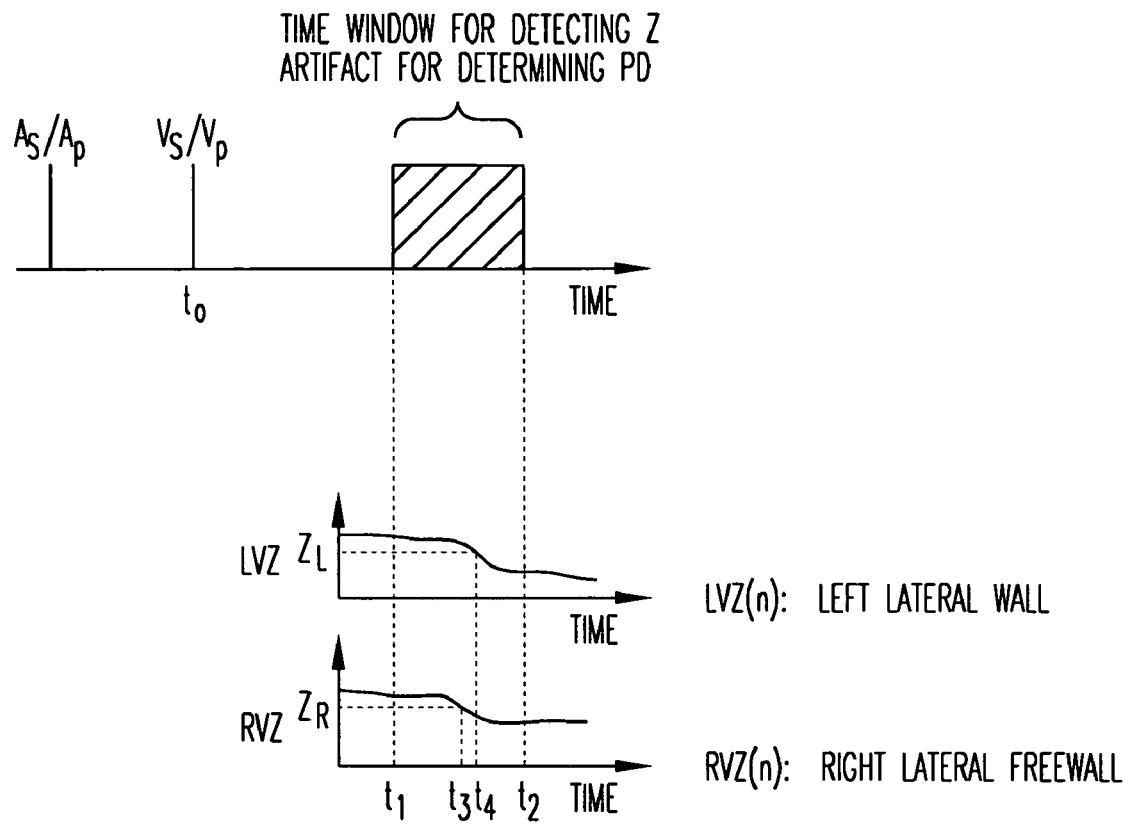
FIG. 8 is a conceptualized (not real data) signal diagram illustrating an embodiment in which a time window is established for identifying an impedance artifact.

In one embodiment, in order to better identify a like impedance artifact in each of the RVZ and LVZ signals for obtaining the phase difference, the zero-crossing, peak-detect, level-detect, etc. is performed during a particular time window portion of the cardiac cycle. In one example, this is accomplished by establishing such a time window relative to a QRS complex or other electrical artifact as detected by the depolarization detector 610, as illustrated in the conceptualized (not real data) signal diagram of FIG. 8. In FIG. 8, a time window between $t_1$ and $t_2$ is triggered following predetermined delay from a ventricular sense ($V_S$) QRS complex or ventricular pace at time to. During the time window, the LVZ and RVZ are examined for the occurrence of a particular impedance artifact. In the illustrated conceptual example, the impedance artifact is an LVZ falling below a certain threshold value $Z_L$ (which occurs, in this example, at time $t_4$) and a corresponding RVZ falling below a corresponding threshold value $Z_R$ (which occurs, in this example, at time $t_3$). In this example, the PD magnitude is $t_4$-$t_3$ with RVZ leading.

In FIG. 7, at 704 if PD indicates that the right ventricle is leading by more than a threshold value (PDT+), then at 706, the AV delay is shortened by a small incremental value, which tends to reduce the amount by which the right ventricle leads the left ventricle. Otherwise, at 708, if the PD indicates that the left ventricle is leading by more than a threshold value (PDT−), then at 710, the AV delay is lengthened by a small incremental value, which tends to reduce the amount by which the left ventricle leads the right ventricle. Otherwise, at 712, if neither the right nor left ventricles is leading by more than its respective threshold, then the AV delay is left unchanged, which tends to leave the synchrony between the left and right ventricles unchanged. The behavior of 704-712 is further understood by reference to the phase delay vs. AV delay graph of FIG. 9. Using PD as an error signal in a closed loop system to control a CRT parameter (such as AV Delay), FIG. 9 illustrates how synchrony between the left and right ventricles is promoted.

Figure 9:
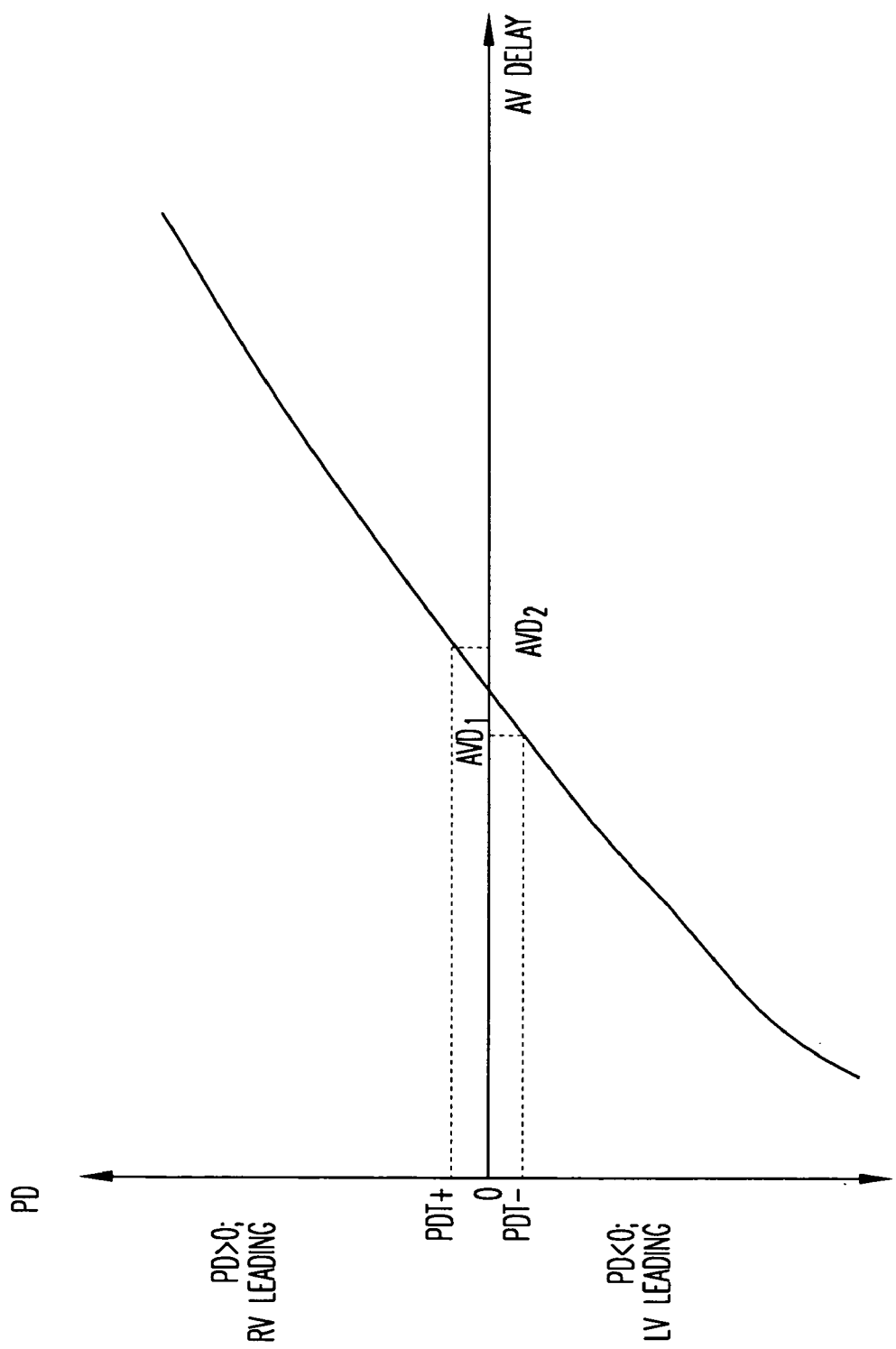
FIG. 9 is a graph of phase delay vs. AV delay.

Although FIGS. 7 and 9 illustrate AV delay as the particular CRT parameter being modified to effect closed-loop control reducing PD, other CRT parameters could similarly be modified to reduce PD. Another example of a CRT parameter is LV offset (LVO), which is the difference between a right ventricular AV delay (AVDR) and a left ventricular AV delay (AVDL). More particularly, LVO=AVDL−AVDR. Therefore, a positive LVO indicates that the right ventricle is programmed to be stimulated earlier than the left ventricle; a negative LVO indicates that the left ventricle is programmed to be stimulated earlier than the right ventricle. In one example, the LVO is adjusted in a closed-loop fashion to reduce the PD error signal, in a similar manner to that illustrated in FIGS. 7 and 9. Similarly, other CRT parameter(s) can be adjusted in a closed-loop fashion to reduce the PD error signal and improve right and left ventricular mechanical synchrony.

The example described above with respect to FIGS. 6-9 reduces the PD by adjusting AV delay or other CRT parameter that improves the spatial coordination of heart contractions without necessarily affecting the cardiac rate. However, as the cardiac rate changes (e.g., from the patient exercising), adjusting the AV delay or other CRT parameter in a closed-loop fashion on a beat-by-beat basis may reduce the PD at such other heart rates. These techniques are expected to be useful for CHF patients with or without electrical conduction disorder, because they focus on a control parameter that is not derived from intrinsic electrical heart signals, but instead use impedance indicative of a mechanical contraction parameter. For this reason, these techniques are also particularly useful for a patient with complete AV block, in which intrinsic electrical signals are not conducted to the ventricles and, therefore, CRT control techniques involving QRS width or other electrical parameters would be unavailable. For similar reasons, these techniques are useful even for patients who manifest a narrow QRS width, for whom QRS width would not be effective as a CRT control parameter.

EXAMPLE 3

Figure 10:
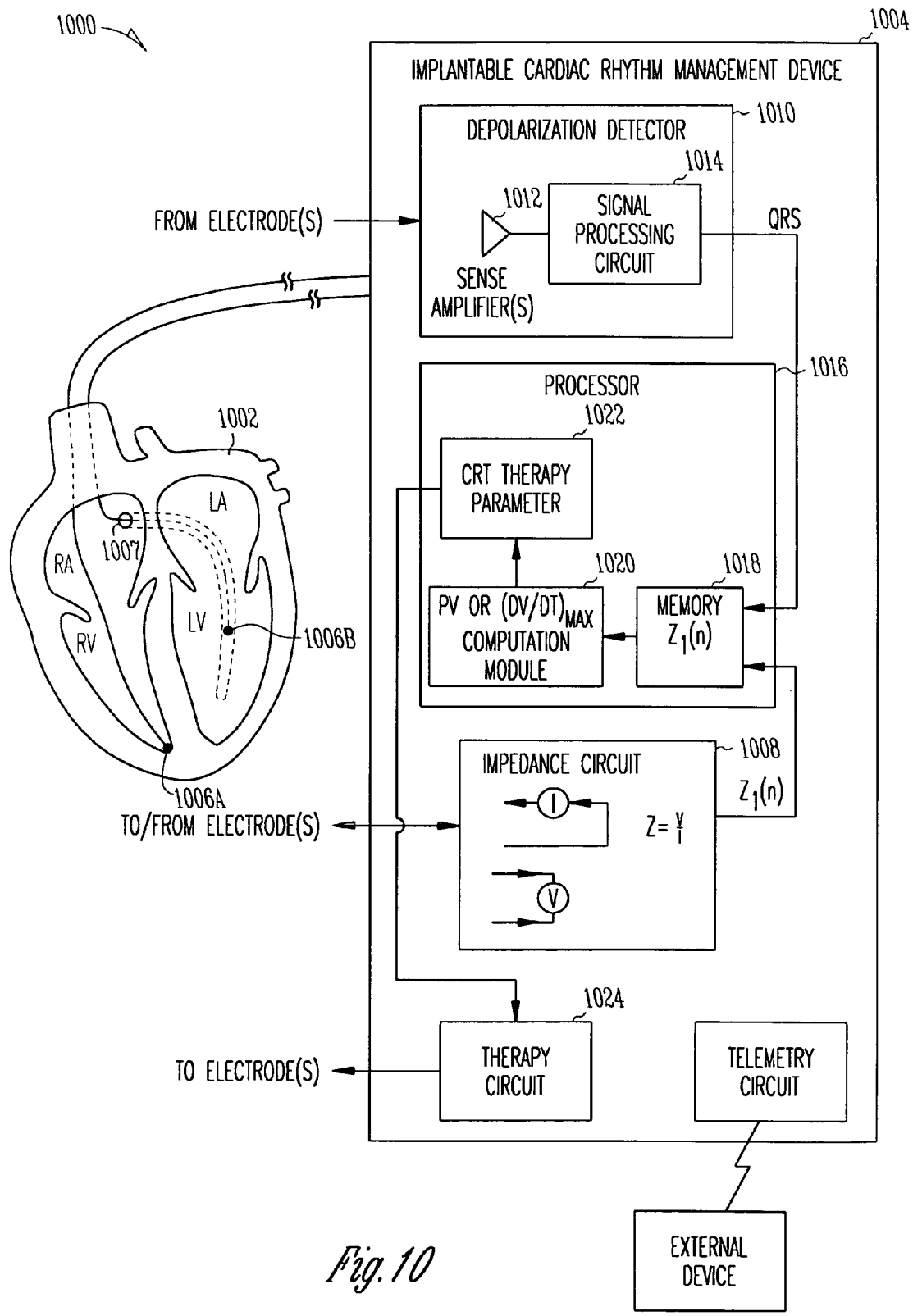
FIG. 10 is a schematic diagram illustrating generally one example of portions of a system and portions of an environment with which it is used.

FIG. 10 is a schematic diagram illustrating generally one example of portions of a system 1000 and portions of an environment with which it is used, including a heart 1002. In this example, the system 1000 includes an implantable cardiac function management device 1004. In one example, the device 1004 is coupled to the heart 1002 using one or more intravascular or other leads. The leads provide electrodes 1006 in association with the heart 1002. FIG. 10 illustrates an example that includes a first electrode 1006A that is located at or near a middle or apical portion of a right ventricular septum, a second electrode 1006B that is located in association with a left ventricular freewall, such as by being introduced on an intravascular lead that is inserted into coronary sinus 1007 toward a lateral or posterior coronary sinus vein.

In FIG. 10, the device 1004 includes an impedance circuit 1008 for measuring a left ventricular impedance between the first electrode 1006A and the second electrode 1006B. The left ventricular impedance is modulated as the left ventricle contracts and expands. In one example, this impedance modulation is used to control a cardiac resynchronization therapy (CRT) parameter, as discussed below.

In the example of FIG. 10, a depolarization detector circuit 1010 detects intrinsic electrical heart depolarizations, such as by using one or more sense amplifiers 1012 or signal processing circuits 1014 to detect QRS complexes, which are depolarizations corresponding to ventricular heart contractions. The time interval between two successive QRS complexes can be used to define a cardiac cycle. In one example, the impedance modulation is monitored over all or a particular desired portion of a cardiac cycle for making the asynchrony determination, as discussed below.

In the example of FIG. 10, a microprocessor, microcontroller, or other processor circuit 1016 executes instructions to provide computational ability. The impedance circuit 1008 provides a sampled data ventricular impedance waveform $Z_1(n)$ to the processor 1016 to be stored in a memory circuit 1018 located within or external to the processor 1016. In this illustrative example, the sampled data ventricular impedance waveform $Z_1(n)$ is a left ventricular impedance. However, it is understood that this technique could alternatively be implemented using a right ventricular impedance waveform $Z_1(n)$.

In one example, the processor 1016 samples a cardiac cycle's worth of the left ventricular impedance waveform $Z_1(n)$ to compute one or both of: (1) an impedance-indicated peak-to-peak volume (PV) indication of the left ventricle; or (2) an impedance-indicated maximum rate of change in left ventricular volume (($dV/dt)_{max}$), as discussed below. In one example, the PV or $(dV/dt)_{max}$ is provided by a peak volume (PV) or $(dV/dt)_{max}$ computation module 1020 comprising instructions that are executed by the processor 1016. In a further example, the PV or $(dV/dt)_{max}$ is used to control at least one cardiac resynchronization therapy (CRT) parameter 1022 such that it tends to increase PV or $(dV/dt)_{max}$. The CRT parameter 1022, in turn, controls one or more aspects of the delivery of stimulation pulses or other CRT therapy by therapy circuit 1024, which is coupled to electrodes associated with the heart 1002, such as electrodes 1006 or other electrodes.

Impedance measurement circuit 1008 can be implemented in a number of different ways, such as by using circuits and techniques similar to those used for detecting transthoracic impedance, an example of which is described in Hartley et al. U.S. Pat. No. 6,076,015, which is incorporated herein by reference in its entirety, including its description of impedance measurement. The Hartley et al. U.S. Pat. No. 6,076,015 describes, among other things, injecting a four-phase carrier signal through two electrodes, such as the present electrodes 1006A and 1006B. Hartley et al. uses first and third phases that are +320 microampere pulses, which are 20 microseconds long. The second and fourth phases are −320 microampere pulses that are 20 microseconds long. The four phases are repeated at 50 millisecond intervals to provide a carrier test current signal from which a responsive voltage can be measured. However, different excitation frequency, amplitude, and pulse duration can also be used. These impedance testing parameters are typically selected to be subthreshold, that is, to avoid evoking a responsive heart contraction. These impedance testing parameters are also typically selected to avoid introducing a visible artifact on an ECG signal monitor.

The Hartley et al. U.S. Pat. No. 6,076,015 describes an exciter circuit for delivering such a test current stimulus (however, the present system can alternatively use other suitable circuits, including an arbitrary waveform generator that is capable of operating at different frequencies or of mixing different frequencies to generate an arbitrary waveform). It also describes a signal processing circuit for measuring a responsive voltage, such as between the present electrodes 1006A and 1006B. In one example, the signal processing circuit includes a preamplifier, demodulator, and bandpass filter for extracting the impedance data from the carrier signal, before conversion into digital form by an A/D converter. Further processing is performed digitally, and is performed differently in the present system 1000 than in the Hartley et al. U.S. Pat. No. 6,076,015. The impedance circuit 1008 of the present system typically includes a digital filter that passes frequency components of the measured impedance signal that are close to the frequency of heart contractions. The digital filter typically attenuates other lower or higher frequency components of the measured impedance signal.

Figure 11:
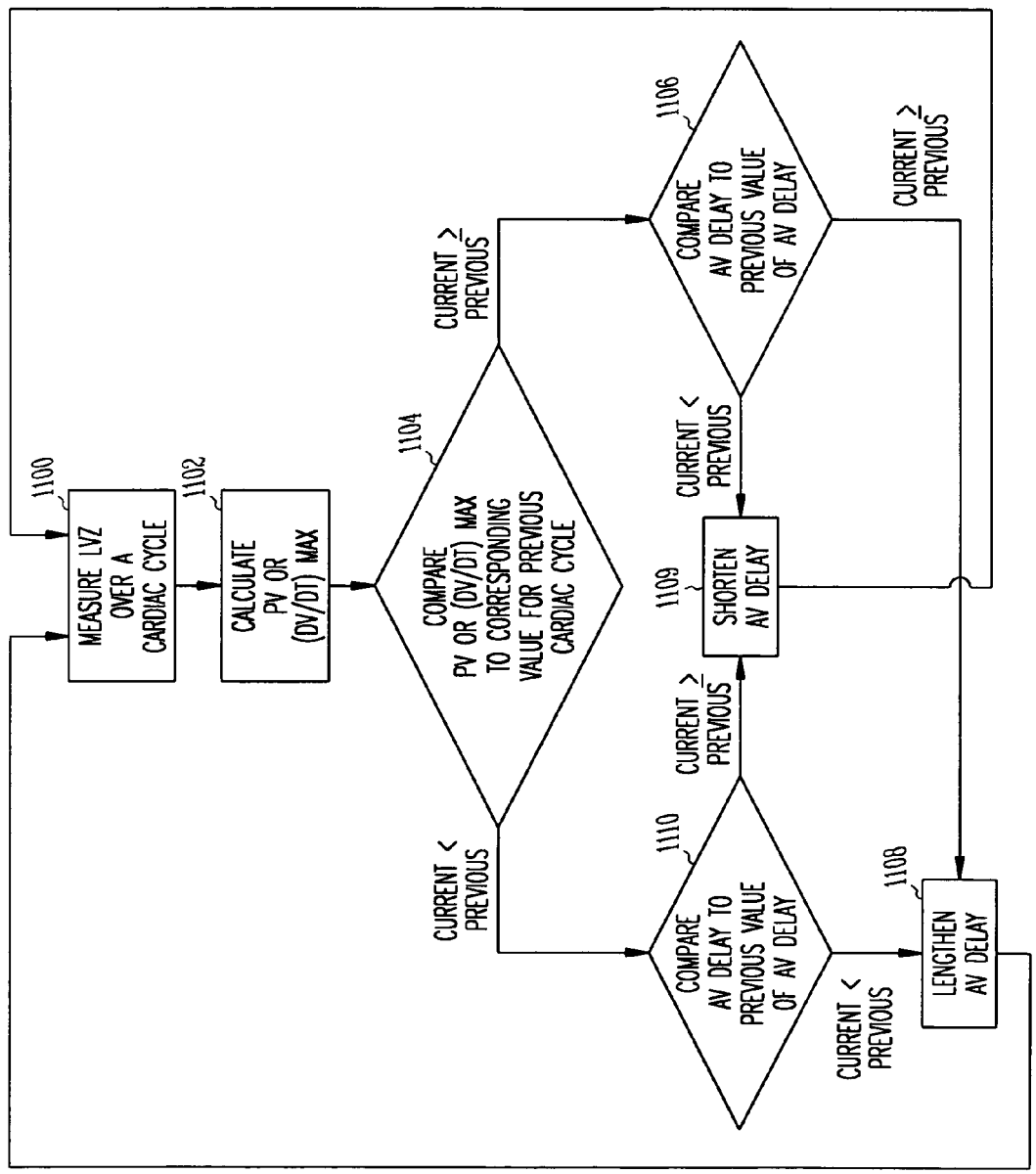
FIG. 11 is a flow chart illustrating generally one example of a technique for controlling a cardiac resynchronization therapy (CRT) parameter in a way that tends to increase an impedance-based indication of peak-to-peak volume (PV) or $(dV/dt)_{max}$.

FIG. 11 is a flow chart illustrating generally one example of a technique for controlling a cardiac resynchronization therapy (CRT) parameter in a way that tends to increase an impedance-based indication of PV or $(dV/dt)_{max}$. At 1100, a left ventricular impedance (LVZ) is monitored over a cardiac cycle, such as by injecting a subthreshold (i.e., non-contraction-evoking) current (e.g., between electrodes 1006A-B) and measuring a responsive voltage (e.g., using electrodes 1006A-B).

At 1102, a peak-to-peak volume (PV) or $(dV/dt)_{max}$ is calculated using the LVZ signal. At 1104 one of the (PV) or $(dV/dt)_{max}$ is compared to its corresponding value for the previous cardiac cycle. If the current value equals or exceeds the previous value, then at 1106 the current AV delay is compared to an AV delay from the previous cardiac cycle (or an averaged or filtered value over several such prior cardiac cycles). If, at 1106, the current AV delay equals or exceeds the previous AV delay, then at 1108, the AV delay is lengthened slightly for the next cardiac cycle and process flow returns to 1100. Otherwise, at 1106, if the current AV delay is less than the previous AV delay, then the AV delay is shortened slightly at 1109 for the next cardiac cycle and process flow returns to 1100.

At 1104, if the current value is less than the previous value, then at 1110. The current AV delay is compared to an AV delay from the previous cardiac cycle (or an averaged or filtered value over several such prior cardiac cycles). If, at 1110, the current AV delay equals or exceeds the previous AV delay, then the AV delay is shortened slightly for the next cardiac cycle at 1109 and process flow returns to 1100. Otherwise, at 1110, if the current AV delay is less than the previous AV delay, then at 1108 the AV delay is lengthened slightly for the next cardiac cycle and process flow returns to 1100.

Figure 12A:
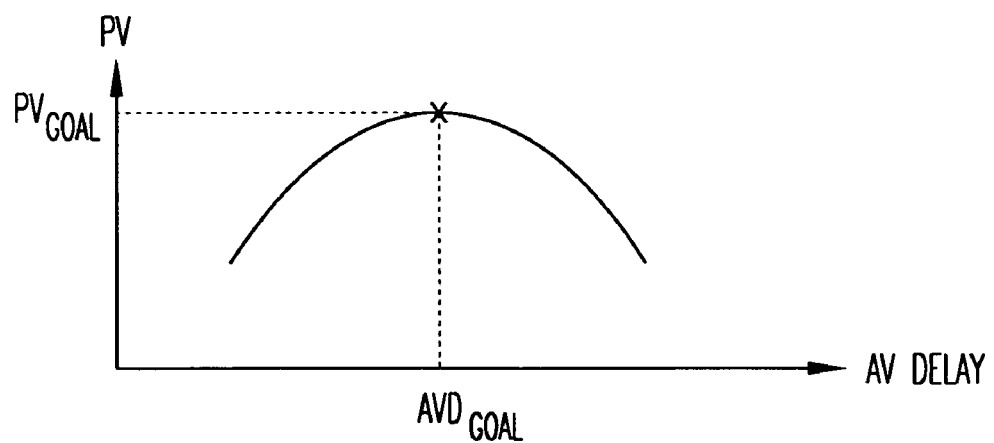
FIG. 12A is a graph of peak-to-peak volume (PV) vs. AV Delay.
Figure 12B:
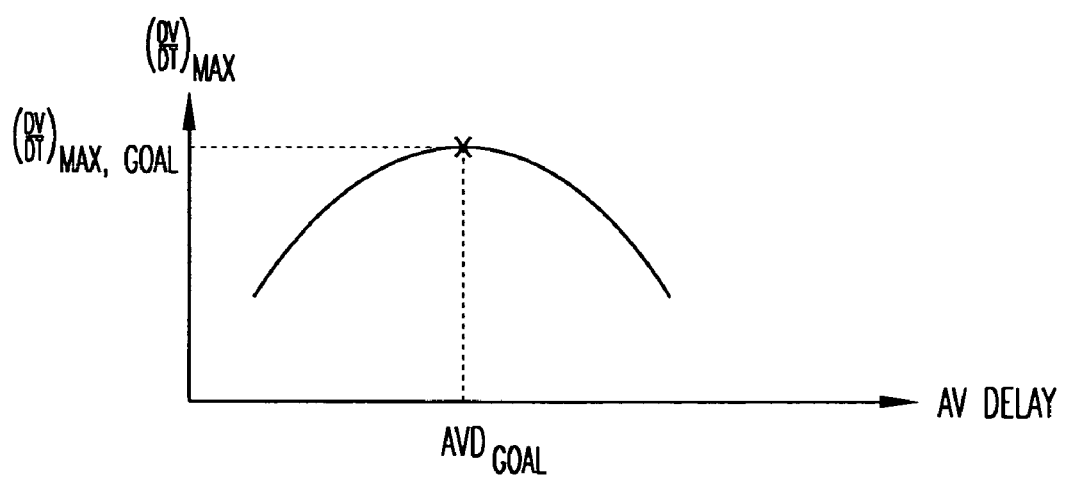
FIG. 12B is a graph of $(dV/dt)_{max}$ vs. AV Delay.

Thus, in the example of FIG. 11, a CRT parameter such as AV delay is adjusted in such a way that it tends to increase PV or $(dV/dt)_{max}$, as illustrated conceptually in the graphs of FIGS. 12A and 12B. In another embodiment, the CRT parameter is adjusted in such a way that it tends to increase a weighted measure of both PV and $(dV/dt)_{max}$. Similarly, other CRT parameter(s) can be adjusted in a closed-loop fashion to increase PV or $(dV/dt)_{max}$. In FIG. 11, each condition (current=previous) can alternatively be associated with (current<previous), instead of being associated with (current>previous), as indicated in the example of FIG. 11.

Figure 13:
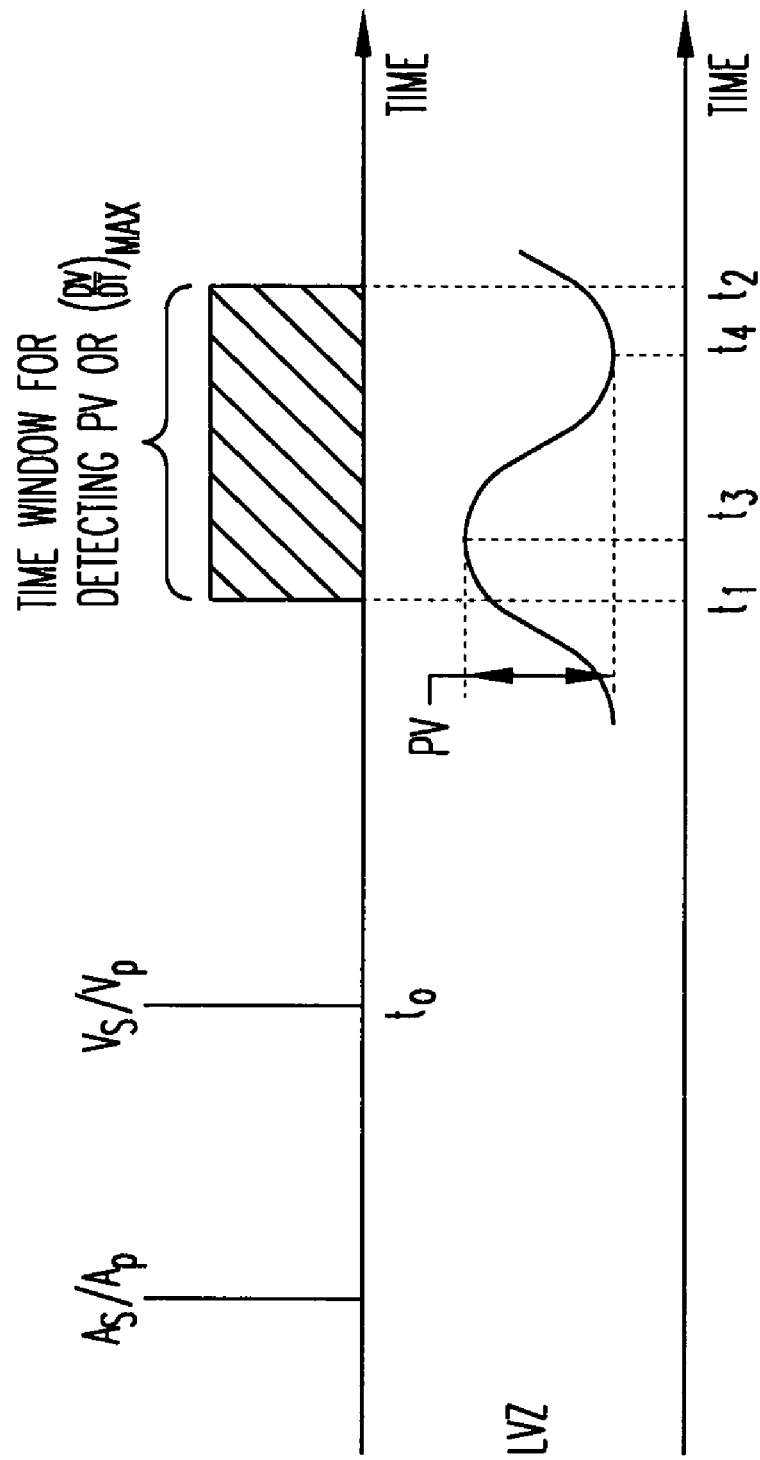
FIG. 13 is a conceptualized (not real data) signal diagram illustrating an embodiment in which a time window is established for measuring the peak-to-peak volume (PV) or $(dV/dt)_{max}$.

In one embodiment, in order to better identify the desired control parameter(s) PV or $(dV/dt)_{max}$, the peak-to-peak or slope measurement is performed during a particular time window portion of the cardiac cycle. In one example, this is accomplished by establishing such a time window relative to a QRS complex or other electrical artifact as detected by the depolarization detector 1010, as illustrated in the conceptualized (not real data) signal diagram of FIG. 13. In FIG. 13, a time window between $t_1$ and $t_2$ is triggered following predetermined delay from a ventricular sense $(V_S)$ QRS complex or ventricular pace $(V_P)$ at time $t_0$. During the time window, the LVZ limits the time period for measuring the control parameter PV or $(dV/dt)_{max}$. In the illustrated conceptual example, the PV is measured between times $t_3$ and $t_4$, which correspond to maximum and minimum values of the LVZ, respectively.

EXAMPLE 4

Figure 14:
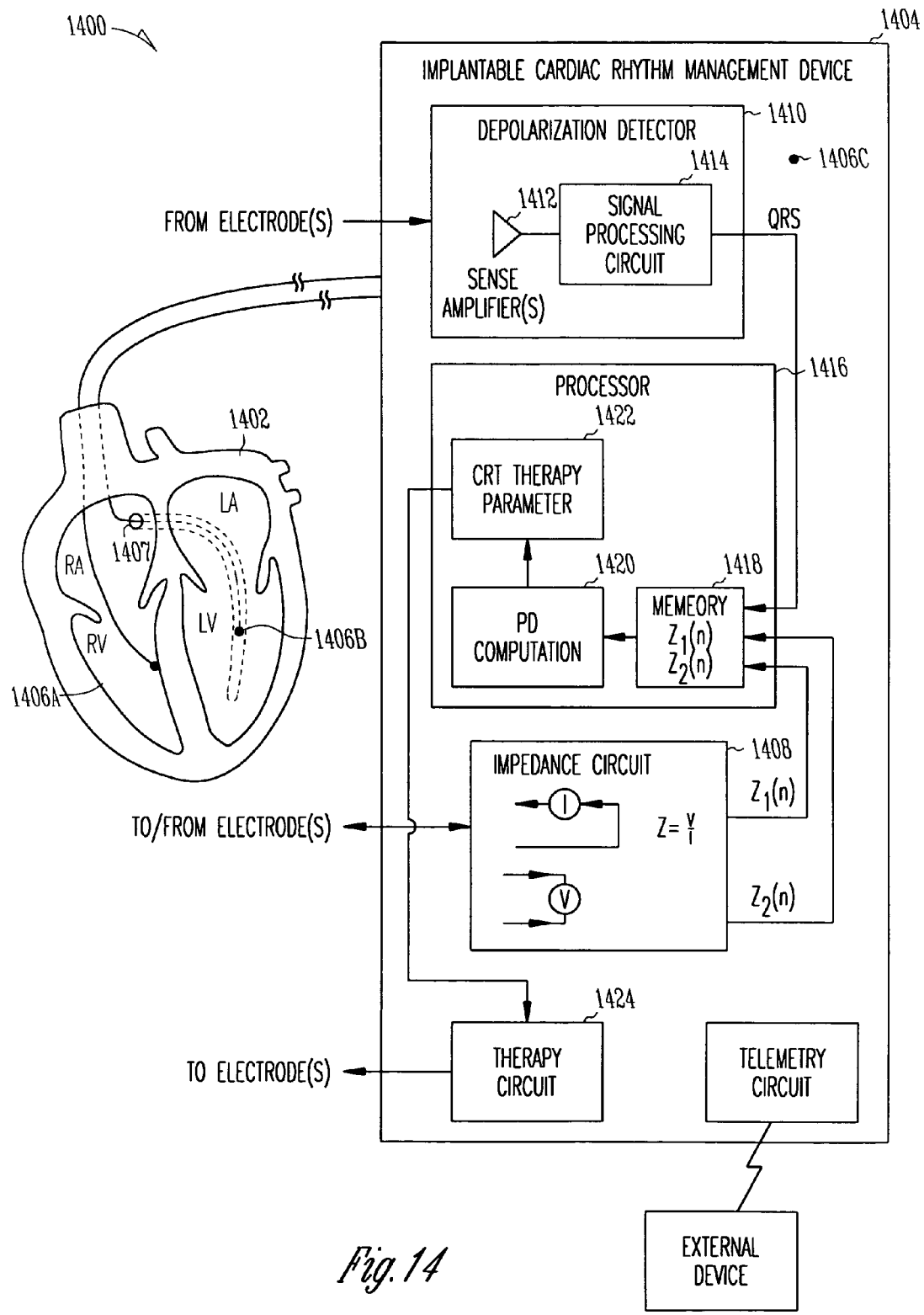
FIG. 14 is a schematic diagram illustrating generally one example of portions of a system and portions of an environment with which it is used.

FIG. 14 is a schematic diagram illustrating generally one example of portions of a system 1400 and portions of an environment with which it is used, including a heart 1402. In this example, the system 1400 includes an implantable cardiac function management device 1404. In one example, the device 1404 is coupled to the heart 1402 using one or more intravascular or other leads. The leads provide electrodes 1406 in association with the heart 1402. FIG. 14 illustrates an example that includes a first electrode 1406A that is located at or near a midportion of a right ventricular septum, a second electrode 1406B that is located in association with a left ventricular freewall, such as by being introduced on an intravascular lead that is inserted into coronary sinus 1407 toward a coronary sinus vein. A third electrode 1406C is located on a hermetically-sealed housing ("can") of the implantable device 1404 (or, alternatively, on an insulating "header" extending from the housing of the implantable device 1404).

In FIG. 14, the device 1404 includes an impedance-circuit 1408 for measuring a first impedance between the first electrode 1406A and the third electrode 1406C and a second impedance between the second electrode 1406B and the third electrode 1406C). The first and second impedances are modulated as the septum and freewall portions of the left ventricle contract and expand. In one example, this impedance modulation is used to detect asynchrony between two different locations associated with the left ventricle, as discussed below.

In the example of FIG. 14, a depolarization detector circuit 1410 detects intrinsic electrical heart depolarizations, such as by using one or more sense amplifiers 1412 or signal processing circuits 1414 to detect QRS complexes, which are depolarizations corresponding to ventricular heart contractions.

The time interval between two successive QRS complexes can be used to define a cardiac cycle. In one example, the impedance modulation is monitored over all or a particular desired portion of a cardiac cycle for making the asynchrony determination, as discussed below.

In the example of FIG. 14, a microprocessor, microcontroller, or other processor circuit 1416 executes instructions to provide computational ability. The impedance circuit 1408 provides a sampled data first ventricular impedance waveform $Z_1(n)$ and a sampled data second ventricular impedance waveform $Z_2(n)$ to the processor 1416 to be stored in a memory circuit 1418 located within or external to the processor 1416. In one example, the processor 1416 samples at least a portion of a cardiac cycle's worth of the first ventricular impedance waveform $Z_1(n)$ and of the second ventricular impedance waveform $Z_2(n)$ to compute an indication of the degree of asynchrony (or, conversely, of synchrony) between the first (e.g., septal) and second (e.g., freewall) portions of the left ventricle, as discussed below. In one example, this indication is provided by a phase difference (PD) computation module 1420 comprising instructions that are executed by the processor 1416. In a further example, the PD or other indication of asynchrony or synchrony is used to control at least one cardiac resynchronization therapy (CRT) parameter 1422. The CRT parameter 1422, in turn, controls one or more aspects of the delivery of stimulation pulses or other CRT therapy by therapy circuit 1424, which is coupled to electrodes associated with the heart 1402, such as electrodes 1406 or other electrodes.

Impedance measurement circuit 1408 can be implemented in a number of different ways, such as by using circuits and techniques similar to those used for detecting transthoracic impedance, an example of which is described in Hartley et al. U.S. Pat. No. 6,076,015, which is incorporated herein by reference in its entirety, including its description of impedance measurement. The Hartley et al. U.S. Pat. No. 6,076,015 describes, among other things, injecting a four-phase carrier signal through two electrodes, such as the present electrodes 1406A and 1406C, or the present electrodes 1406B and 1406C. Hartley et al. uses first and third phases that are +320 microampere pulses, which are 20 microseconds long. The second and fourth phases are –320 microampere pulses that are 20 microseconds long. The four phases are repeated at 50 millisecond intervals to provide a carrier test current signal from which a responsive voltage can be measured. However, different excitation frequency, amplitude, and pulse duration can also be used. These impedance testing parameters are typically selected to be subthreshold, that is, to avoid evoking a responsive heart contraction. These impedance testing parameters are also typically selected to avoid introducing a visible artifact on an ECG signal monitor.

The Hartley et al. U.S. Pat. No. 6,076,015 describes an exciter circuit for delivering such a test current stimulus (however, the present system can alternatively use other suitable circuits, including an arbitrary waveform generator that is capable of operating at different frequencies or of mixing different frequencies to generate an arbitrary waveform). It also describes a signal processing circuit for measuring a responsive voltage, such as between the present electrodes 1406A and 1406C, or between the present electrodes 1406B and 1406C. In one example, the signal processing circuit includes a preamplifier, demodulator, and bandpass filter for extracting the impedance data from the carrier signal, before conversion into digital form by an A/D converter. Further processing is performed digitally, and is performed differently in the present system 1400 than in the Hartley et al. U.S. Pat. No. 6,076,015. The impedance circuit 1408 of the present system typically includes a digital filter that passes frequency components of the measured impedance signal that are close to the frequency of heart contractions. The digital filter typically attenuates other lower or higher frequency components of the measured impedance signal.

Figure 15:
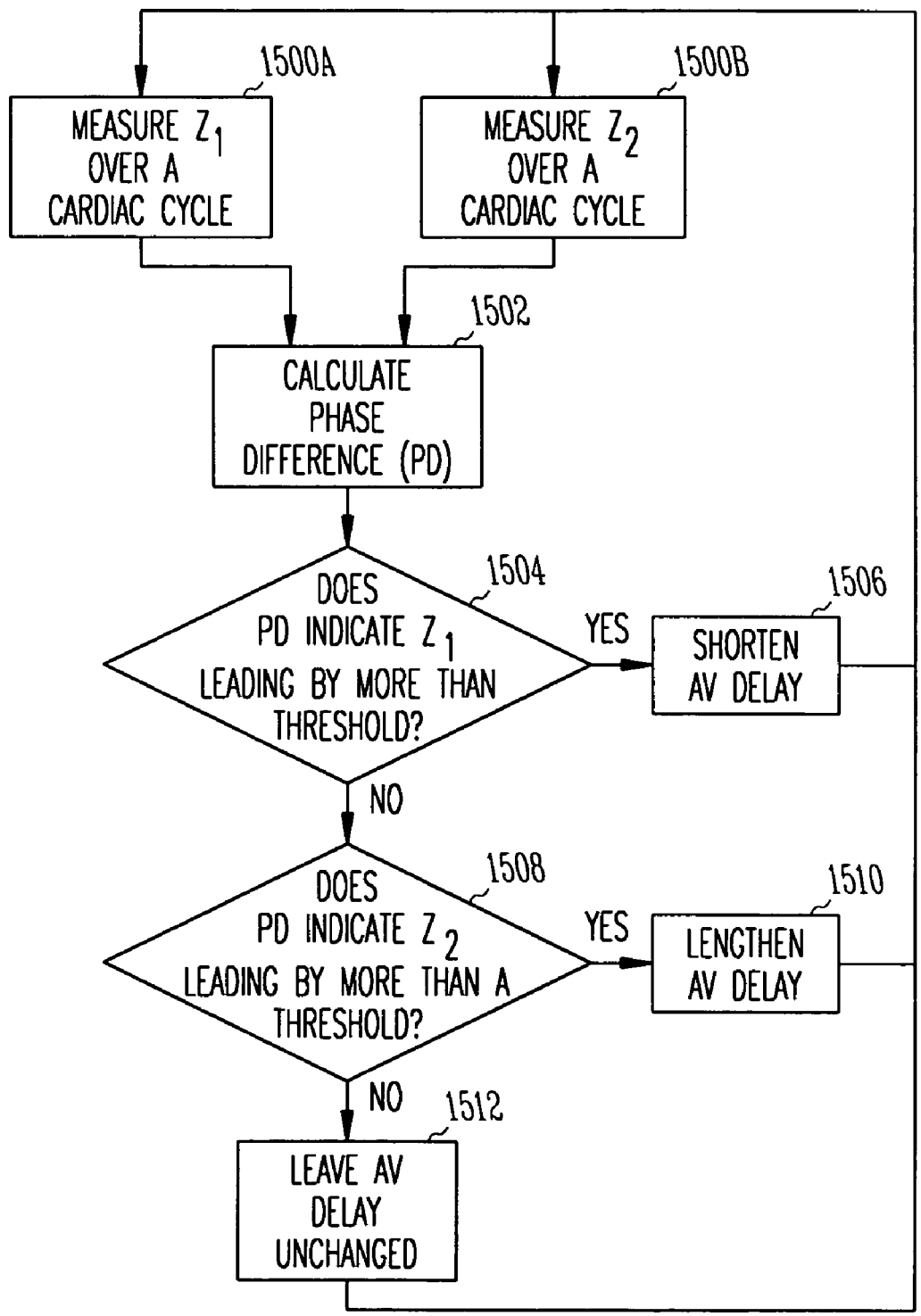
FIG. 15 is a flow chart illustrating generally one example of a technique for determining a degree of synchrony or asynchrony between septal and left ventricular freewall portions of a heart.

FIG. 15 is a flow chart illustrating generally one example of a technique for determining a degree of synchrony or asynchrony between first and second locations of left ventricular contractions of a heart. At 1500A, a first ventricular impedance ($Z_1$) is monitored over a cardiac cycle, such as by injecting a subthreshold (i.e., non-contraction-evoking) current (e.g., between electrodes 1406A and 1406C) and measuring a responsive voltage (e.g., using electrodes 1406A and 1406C). Concurrent with 1500A, at 1500B, a second ventricular impedance ($Z_2$) is monitored over the same cardiac cycle, such as by injecting a subthreshold current (e.g., between electrodes 1406B and 1406C) and measuring a responsive voltage (e.g., using electrodes 1406B and 1406C).

At 1502, a phase difference (PD) between the first and second locations of the ventricular contractions is calculated using $Z_1$ and $Z_2$. In one embodiment, the phase difference is calculated by measuring a time difference between the same artifact on each of the $Z_1$ and Zhd 2 l signals. In one example, a zero-cross detector detects a like zero-crossing artifact in each of the $Z_1$ and $Z_2$ signals, and PD is then calculated as the time difference between occurrences of these two like zero-crossings. In another example, a peak-detector detects a like peak artifact in each of the $Z_1$ and $Z_2$ signals, and PD is then calculated as the time difference between occurrences of these two like peaks. In yet another example, a level-detector detects a like level in each of the $Z_1$ and $Z_2$ signals, and PD is then calculated as a time difference between the occurrences of these two like signal levels.

Figure 16:
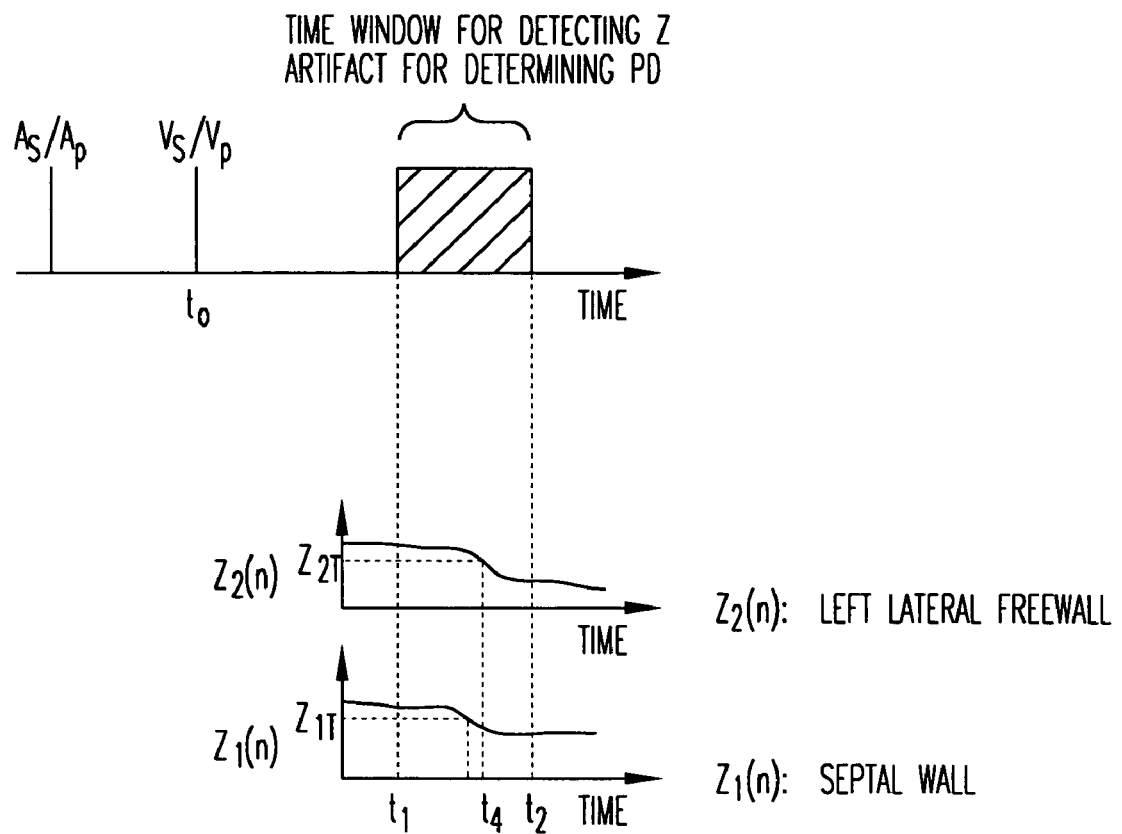
FIG. 16 is a conceptualized (not real data) signal diagram illustrating an embodiment in which a time window is established for identifying an impedance artifact.

In one embodiment, in order to better identify a like impedance artifact in each of the $Z_1$ and $Z_2$ signals for obtaining the phase difference, the zero-crossing, peak-detect, level-detect, etc. is performed during a particular time window portion of the cardiac cycle. In one example, this is accomplished by establishing such a time window relative to a QRS complex or other electrical artifact as detected by the depolarization detector 1410, as illustrated in the conceptualized (not real data) signal diagram of FIG. 16. In FIG. 16, a time window between $t_1$ and $t_2$ is triggered following predetermined delay from a ventricular sense ($V_S$) QRS complex or ventricular pace at time to. During the time window, the $Z_1$ and $Z_2$ signals are examined for the occurrence of a particular impedance artifact. In the illustrated conceptual example, the impedance artifact is an $Z_2$ falling below a certain threshold value $Z_{2T}$ (which occurs, in this example, at time $t_4$) and a corresponding $Z_1$ falling below a corresponding threshold value $Z_{1T}$ (which occurs, in this example, at time $t_3$). In this example, the PD magnitude is $t_4$-$t_3$ with $Z_1$ (septum) leading $Z_2$ (LV freewall).

In FIG. 15, at 1504 if PD indicates that $Z_1$ (the septum) is leading $Z_2$ (the left ventricular freewall) by more than a threshold value (PDT+), then at 1506, the AV delay is shortened by a small incremental value, which tends to reduce the amount by which the septum leads the left ventricular freewall. Otherwise, at 1508, if the PD indicates that $Z_2$ (the left ventricular freewall) is leading $Z_1$ (the septum) by more than a threshold value (PDT–), then at 1510, the AV delay is lengthened by a small incremental value, which tends to reduce the amount by which the left ventricular freewall leads the septum. Otherwise, at 1512, if neither $Z_1$ (septum) or $Z_2$ (left ventricular freewall) is leading by more than its respective threshold, then the AV delay is left unchanged, which tends to leave the synchrony between the septum and the left ventricular freewall unchanged. The behavior of 1504-1512 is further understood by reference to the phase delay vs. AV delay graph of FIG. 17. Using PD as an error signal in a closed loop system to control a CRT parameter (such as AV Delay), FIG. 17 illustrates how synchrony between the septum and left ventricular freewall is promoted.

Figure 17:
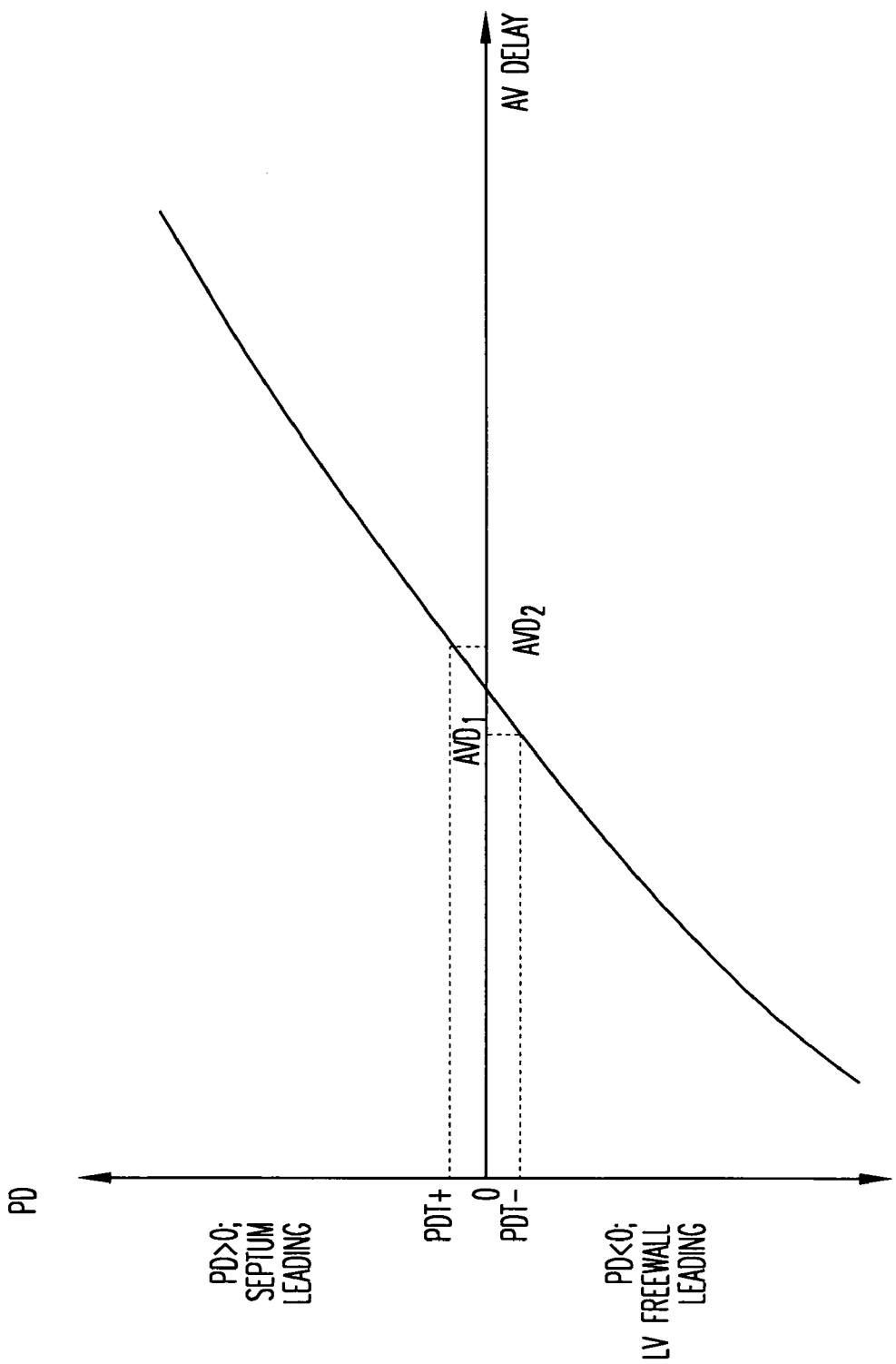
FIG. 17 is a graph of phase delay vs. AV delay.

Although FIGS. 15 and 17 illustrate AV delay as the particular CRT parameter being modified to effect closed-loop control reducing PD, other CRT parameters could similarly be modified to reduce PD. Another example of a CRT parameter is LV offset (LVO), which is the difference between a right ventricular AV delay (AVDR) and a left ventricular AV delay (AVDL). More particularly, LVO=AVDL−AVDR. Therefore, a positive LVO indicates that the right ventricle is programmed to be stimulated earlier than the left ventricle; a negative LVO indicates that the left ventricle is programmed be stimulated earlier than the right ventricle. In one example, the LVO is adjusted in a closed-loop fashion to reduce the PD error signal between the septum and the left ventricular freewall, in a similar manner to that illustrated in FIGS. 15 and 17. Similarly, other CRT parameter(s) can be adjusted in a closed-loop fashion to reduce the PD error signal and improve right and left ventricular mechanical synchrony.

The example described above with respect to FIGS. 14-17 reduces the PD by adjusting AV delay or other CRT parameter that improves the spatial coordination of heart contractions without necessarily affecting the cardiac rate. However, as the cardiac rate changes (e.g., from the patient exercising), adjusting the AV delay or other CRT parameter in a closed-loop fashion on a beat-by-beat basis may reduce the PD at such other heart rates. These techniques are expected to be useful for CHF patients with or without electrical conduction disorder, because they focus on a control parameter that is not derived from intrinsic electrical heart signals, but instead use impedance indicative of a mechanical contraction parameter. For this reason, these techniques are also particularly useful for a patient with complete AV block, in which intrinsic electrical signals are not conducted to the ventricles and, therefore, CRT control techniques involving QRS width or other electrical parameters would be unavailable. For similar reasons, these techniques are useful even for patients who manifest a narrow QRS width, for whom QRS width would not be effective as a CRT control parameter.

Conclusion

Portions of the above description have emphasized using LVZ to determine the control parameter. This is because, in most CHF patients, enlargement occurs in the left ventricle, and therefore, cardiac resynchronization therapy is most effective when used to help control left ventricular cardiac output. However, in some patients, enlargement occurs in the right ventricle instead of the left ventricle. For such patients, the cardiac resynchronization techniques described above can be applied analogously to the right ventricle, or to both ventricles.

At least some of the examples described above with improve the stroke volume of a ventricle by adjusting AV delay or other CRT parameter that improves the spatial coordination of heart contractions without necessarily affecting the cardiac rate. However, as the cardiac rate changes (e.g., from the patient exercising), adjusting the AV delay or other CRT parameter in a closed-loop fashion on a beat-by-beat basis may improve the stroke volume at such other heart rates. These techniques are expected to be useful for CHF patients with or without electrical conduction disorder, because they focus on a control parameter that is not derived from intrinsic electrical heart signals, but instead use impedance indicative of a mechanical contraction parameter. For this reason, these techniques are also particularly useful for a patient with complete AV block, in which intrinsic electrical signals are not conducted to the ventricles and, therefore, CRT control techniques involving QRS width or other electrical parameters would be unavailable. For similar reasons, these techniques are useful even for patients who manifest a narrow QRS width, for whom QRS width would not be effective as a CRT control parameter.

Although the above examples have emphasized beat-by-beat closed-loop control of CRT parameters, it is understood that such techniques are also applicable to providing useful information to a physician or other caregiver to help guide the appropriate programming of one or more CRT parameters.

The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

Such embodiments of the inventive subject matter may be referred to herein, individually and/or collectively, by the term "invention" merely for convenience and without intending to voluntarily limit the scope of this application to any single invention or inventive concept if more than one is in fact disclosed. Thus, although specific embodiments have been illustrated and described herein, it should be appreciated that any arrangement calculated to achieve the same purpose may be substituted for the specific embodiments shown. This disclosure is intended to cover any and all adaptations, or variations, or combinations of various embodiments. Combinations of the above embodiments, and other embodiments not specifically described herein, will be apparent to those of skill in the art upon reviewing the above description.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separate embodiment.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the present document, including in the following claims, the terms "first," "second," and "third," etc. are used merely as labels, and are not intended to impose numerical requirements on their objects.

What is claimed is:

1. A machine-assisted method comprising:
   measuring a first impedance signal, the first impedance signal being substantially indicative of a volume of a first ventricle of a heart as the first ventricle expands and contracts during a cardiac cycle of the heart;
   measuring a second impedance signal, the second impedance signal being substantially indicative of a volume of a second ventricle, different from the first ventricle, as the second ventricle expands and contracts during the same cardiac cycle;
   forming a function that parameterizes the first impedance signal as the function of the second impedance signal during the same cardiac cycle, the forming the first function includes forming a Lissajous function that parameterizes the first impedance signal as the function of the second impedance signal during the same cardiac cycle, the Lissajous function enclosing a loop area during the cardiac cycle; and
   computing an indication of a degree of synchrony or asynchrony between the right and left ventricles using an indication of the loop area wherein computing the degree of synchrony or asynchrony includes:
   computing a rectangular area defined by maximum and minimum impedances of each of the first and second ventricles during the cardiac cycle; and
   computing a synchronization fraction by forming a difference of the rectangular area less the loop area, and dividing the difference by the rectangular area.

2. The method of claim 1, in which:
   the measuring the first impedance signal includes using a first electrode in a right atrium and a second electrode in a right ventricle; and
   the measuring the second impedance signal includes using the first electrode and a third electrode introduced into a coronary sinus vein such that the third electrode is in association with a left ventricular freewall.

3. The method of claim 1, in which:
   the measuring the first impedance signal includes using a first electrode in a right atrium and a second electrode in a right ventricle; and
   the measuring the second impedance signal includes using a third electrode introduced into a coronary sinus vein such that the third electrode is in association with a left atrium, and a fourth electrode located in a coronary sinus vein such that the fourth electrode is in association with a left ventricular freewall.

4. The method of claim 1, in which the measuring the first impedance includes using a right ventricular electrode and a reference electrode located on a hermetically sealed housing of an implantable device or located on an insulating header extending from the housing of the implantable device, and in which the measuring the second impedance includes using a left ventricular electrode and a reference electrode located on a hermetically sealed housing of an implantable device or located on an insulating header extending from the housing of the implantable device.

5. The method of claim 1, further comprising:
   automatically adjusting a cardiac resynchronization therapy parameter that synchronizes left and right ventricular heart contractions, using the synchronization fraction, in a way such that the synchronization tends to increase the degree of synchrony or decrease the degree of asynchrony given by the indication.

6. The method of claim 1, further comprising:
   automatically adjusting a cardiac resynchronization therapy parameter, using the indication, in a way that tends to increase the degree of synchrony or decrease the degree of asynchrony given by the indication.

7. The method of claim 6, in which the adjusting the cardiac resynchronization therapy parameter includes adjusting an atrioventricular (AV) delay.

8. The method of claim 6, in which the adjusting the cardiac resynchronization therapy parameter includes adjusting an interventricular delay.

9. The method of claim 6, in which the adjusting the cardiac resynchronization therapy parameter includes adjusting an intraventricular delay.

10. The method of claim 1, further comprising communicating information about the indication of the degree of synchrony or asynchrony from an implantable cardiac rhythm management device.

11. A machine-assisted method comprising:
    measuring a first impedance signal of a first ventricle as the first ventricle expands and contracts during a cardiac cycle, the first impedance signal measured by delivering a current to the first ventricle and measuring a resulting voltage across a first electrode and a second electrode, the first and second electrodes located near opposing sides of the first ventricle;
    measuring a second impedance signal of a second ventricle, different from the first ventricle, as the second ventricle expands and contracts during the same cardiac cycle, the second impedance signal measured by delivering a current to the second ventricle and measuring a resulting voltage across a third electrode and a fourth electrode, the third and fourth electrodes located near opposing sides of the second ventricle;
    forming a Lissajous function that parameterizes the first impedance signal as the function of the second impedance signal during the same cardiac cycle, the Lissajous function enclosing a loop area during the cardiac cycle; and
    automatically adjusting a cardiac resynchronization therapy parameter that synchronizes left and right ventricular heart contractions, the automatically adjusting controlled in a feedback loop manner to decrease the loop area for at least one subsequent cardiac cycle wherein automatically adjusting the cardiac resynchronization therapy parameter to decrease the loop area includes decreasing the loop area relative to a rectangle defined by maximum and minimum impedances of each of the first and second ventricles during the cardiac cycle.

12. A system comprising:
    a device comprising:
    an impedance measurement circuit, including terminals configured to be coupled to electrodes in association with a first ventricle of a heart to measure a first impedance signal that is substantially indicative of a volume of the first ventricle of the heart as the first ventricle expands and contracts during a cardiac cycle of the heart, and in association with a second ventricle of the heart to measure a second impedance signal that is substantially indicative of a volume of the second ventricle of the heart as the second ventricle expands and contracts during the same cardiac cycle of the heart; and a processor circuit, coupled to the impedance measurement circuit to receive information about the first and second impedance signals over the cardiac cycle, the processor performing instructions to form a function that parameterizes the first impedance signal as the function of the second impedance signal during the same cardiac cycle, the forming the first function includes forming a Lissajous function that parameterizes the first impedance signal as the function of the second impedance signal during the same cardiac cycle, the Lissajous function enclosing a loop area during the cardiac cycle, and to compute an indication of a degree of synchrony or asynchrony between the right and left ventricles using an indication of the loop area wherein the instructions performable to compute the degree of synchrony or asynchrony includes:

computing a rectangular area defined by maximum and minimum impedances of each of the first and second ventricles during the cardiac cycle; and computing a synchronization fraction by forming a difference of the rectangular area less the loop area, and dividing the difference by the rectangular area.

13. The system of claim 12, in which the device includes an implantable medical device that further comprises a telemetry circuit, coupled to the processor circuit to receive information about the indication of the degree of synchrony or asynchrony, the telemetry circuit configured to communicate data about the indication of degree of synchrony or asynchrony from the implantable medical device.

14. The system of claim 12, in which the device includes an implantable medical device that further comprises a therapy circuit configured to provide cardiac resynchronization therapy to the heart, the processor adjusting delivery of the cardiac resynchronization therapy in a closed-loop fashion in a way that tends to increase, for at least one subsequent cardiac cycle, the indication of the degree of synchrony computed by the processor circuit or to decrease the indication of the degree of asynchrony computed by the processor circuit.

* * * * *